(12) United States Patent
Qin et al.

(10) Patent No.: US 7,517,676 B2
(45) Date of Patent: Apr. 14, 2009

(54) HUMAN CYCLOOXYGENASE-3 ENZYME AND USES THEREOF

(75) Inventors: Ning Qin, Blue Bell, PA (US); Ellen E. Codd, Blue Bell, PA (US); Christopher Flores, Lansdale, PA (US); Sui-Po Zhang, Bala Cynwyd, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 56 days.

(21) Appl. No.: 11/651,705

(22) Filed: Jan. 10, 2007

(65) Prior Publication Data

US 2007/0166789 A1 Jul. 19, 2007

Related U.S. Application Data

(63) Continuation of application No. 10/783,297, filed on Feb. 20, 2004, now abandoned.

(60) Provisional application No. 60/449,230, filed on Feb. 21, 2003.

(51) Int. Cl.
*C12P 21/06* (2006.01)
*C12N 9/02* (2006.01)
*C12N 15/00* (2006.01)
*C12N 5/02* (2006.01)
*C07H 21/04* (2006.01)

(52) U.S. Cl. .................. 435/189; 435/69.1; 435/320.1; 435/325; 536/23.2

(58) Field of Classification Search ........................ None
See application file for complete search history.

(56) References Cited

U.S. PATENT DOCUMENTS

| 6,432,648 B1 | 8/2002 | Blumenfeld |
| 6,812,339 B1 | 11/2004 | Venter |
| 2003/0220306 A1 | 11/2003 | Simmons |

FOREIGN PATENT DOCUMENTS

| WO | WO 00/47771 A2 | 8/2000 |
| WO | WO 03/029411 A | 4/2003 |

OTHER PUBLICATIONS

Broun et al., Catalytic plasticity of fatty acid modification enzymes underlying chemical diversity of plant lipids. Science, 1998, vol. 282: 1315-1317.*
Witkowski et al., Conversion of b-ketoacyl synthase to a malonyl decarboxylase by replacemnt of the active-site cysteine with glutamine. Biochemistry, 1999, vol. 38: 11643-11650.*
Seffernick et al., Melamine deaminase and Atrazine chlorohydrolase: 98 percent identical but functionally different. J. Bacteriol.,2001, vol. 183 (8): 2405-2410.*
Whisstock et al., Prediction of protein function from protein sequence. Q. Rev. Biophysics., 2003, vol. 36 (3): 307-340.*
Dubois et al., Cyclooxygenase in biology and disease. FASEB Journal, 1998, vol. 12: 1063-1073.*
Wigley et al., Site-specific transgene insertion: an approach. Reprod. Fert. Dev., 1994, vol. 6: 585-588.*
Mullins et al., Transgenesis in nonmurine species. Hypertension, 1993, vol. 22 (4): 630-633.*
Mullins et al., Transgenesis in the rat and larger mammals. J. Clin. Invest., 1996, vol. 97 (7): 1557-1560.*
Kappel et al., Regulating gene expression in transgenic animals. Current Opinion in Biotechnology 1992, vol. 3: 548-553.*
Cameron ER., Recent advances in transgenic technology. 1997, vol. 7: 253-265.*
Chandrasekharan N V et al "COX-3, a cyclooxygenase-1 variant inhibited by acetaminophen and other analgesic/antipyretic drugs: Cloning, structure, and expression" Proc. Natl. Acad. Sci. USA. vol. 99, No. 21. (2002) pp. 13926-13931, XP002293141.
Scott, B.T. et al "Characterization of the Human Prostaglandin H Synthase 1 Gene (PTGS1): Exclusion by Genetic Linkage Analysis as a Second Modifier Gene in Familial Thrombosis" Blood Coagulation and Fibrinolysis. vol. 13, No. 6 (2002) pp. 519-531, XP002293145.
Wang, Lee-Ho et al "Characterization of the Promoter of Human Prostaglandin H Synthase-1 Gene" Biochemical and Biophysical Research Communications. vol. 190, No. 2 (1993) pp. 406-411, XP002293144.
Warner, Timothy D. et al "Cyclooxygenase-3 (COX-3): Filling in the gaps toward a COX Continuum?" Proc. Natl. Acad. Sci. USA vol. 99, No. 21. Oct. 15, 2002. pp. 13371-13373. XP002293142.

* cited by examiner

*Primary Examiner*—Richard Hutson
*Assistant Examiner*—Ganapathirama Raghu

(57) ABSTRACT

The present invention provides nucleic acid and polypeptide sequences describing a neve isozyme of the cyclooxygenase enzyme, herein named as human cyclooxygenase 3. The isolated nucleic acid or polypeptide molecule of the invention can be used in detection assays, gene therapy, and screening assays.

3 Claims, 5 Drawing Sheets

*Exon 1:*
ATG AGC CG

*Exon 2:*
G AGT CTC TTG CTC TGG TTC TTG CTG CTC TTC CTG CTC CCG CGG CTC CCC GTC CTG CTC GCG GAC CCA GGG GCG
CCC ACG CCA G

*Intron 1:*
TGAGTGCGACCCCGGTGCCCGGTGTGGGAATTTTCTTGGCCTCCTGGTGAGCCTTGAATGCCAGGCTCAGCCCCTCATCTCTCTCCTCTGCAGG

B.

```
1       ---------+---------+---------+---------+---------+---------+   60
        TACTCGGCACTCAGCGTGGGCTGGGGCCACGGGCCACCCCTTAAAGAACCGGAGGACCACTCG
        GCCCGGTGGGGAATTTTCTTGGCCTCCTGGTGAGC
           M  S   R   E  C   D   P   G   A   R   W   G   I   F   L   A   S   W   S  -
        *  A  V   S   A   T   P   P   V   P   G   G   E   F   S   W   P   P   G   G   A  -
         E   P   *   V   R   P   R   C   P   V   G   N   F   L   G   L   L   V   E   P  -
                        Exon1    Intron1
61      ---------+---------+---------+---------+---------+---------+  120
        CTTGAATGCCAGGCTCAGCCCCTCATCTCTCTCCTCTGCAGGGAGTCTCTTGCTCTGGTT
        GAACTTACGGTCCGAGTCGGGGAGTAGAGAGAGGAGACGTCCTCAGAGAACGAGACCAA
         L   E   C   Q   A   Q   P   L   I   S   L   L   C   R   E   S   L   A   L   V  -
         L   N   A   R   L   S   P   S   S   L   S   S   A   G   S   L   W   S  -
        *  M  P   G   S   A   P   H   L   S   P   L   Q   G   G   V   S   C   S   G   S  -
                                                                         Exon2
121     ---------+---------+---------+---------+---------+---------+  180
        CTTGCTGTTCCTGCTCCTGCCGCTCCCCGTCCTGCTCGCGGACCCAGGGGCGCC
        GAACGACAAGGACGAGGACGGCGAGGGGCAGGAGGAGCGCC
         L   A   V   P   A   P   A   A   P   R   P   A   R   G   P   R   G   A  -
        C   C   S   C   S   R   R   S   P   S   C   S   R   T   Q   G   R   P  -
```

Figure 1 continued

```
        CACGCCAGGTAG
181     ------+-----
        GTGCGGTCCATC
        H  A  R  *
           R  Q  V
```

C. Human COX-3a

```
        ATGAGCCGTGAGTGCGACCCCGGTGCCCGGTGGGAATTTTCTTGGCCTCCTGGTGAGC
1       ------+---------+---------+---------+---------+---------+    60
        TACTCGGCACTCACGCTGGGGCCACGGGCCACCCCTTAAAAGAACCGGAGACCACTCG
        M  S  R  E  C  D  P  G  A  R  W  G  I  F  L  A  S  W  W  S
              Exon1   Intron1→

CTTGAATGCCAGCTCAGCCCCCATCTCTCCTCTGCAGGGAGTCTCTTGCTCTGGTTC
61      ------+---------+---------+---------+---------+---------+    120
        GAACTTACGGTCGAGTCGGGGAGTAGAGAGGAGACGTCCCTCAGAGAACGAGACCAAG
        L  E  C  Q  L  S  S  S  L  S  S  A  G
                                            Exon2→

TTGCTGTTCCTCCTGCTCCCCGCCCCGCCCCCGCCGCTCCCCGTCCTGGACCCAGGGGCGCCC
121     ------+---------+---------+---------+---------+---------+    180
        AACGACAAGGACGAGGACGAGGGCGGCGAGGGCCGAGGAGCGGCTGGTCCCCGCGGG
        L  L  F  L  L  L  P  P  L  P  P  V  L  L  A  D  P  G  A  P

ACGCCAGGT
181     ------+-----
        TGCGGTCCA
        T  P  G
```

D. Human COX-3b

```
        ATGAGCCGTGAGTGCGACCCCGGTGCCCGGTGGGAATTTTCTTGGCCTCCTGGTGAGCC
1       ------+---------+---------+---------+---------+---------+    60
        TACTCGGCACTCACGCTGGGGCCACGGGCCACCCCTTAAAAGAACCGGAGACCACTCGG
        M  S  R  E  C  D  P  G  A  R  W  G  I  F  L  A  S  G  G  A
                                          Intron1→
```

Figure 1 continued

SEQUENCE LISTING

```
<160> NUMBER OF SEQ ID NOS: 27

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atgagccgtg agtgcgaccc cggt                                             24

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctacctggcg tgggcgcccc tgggt                                            25

<210> SEQ ID NO 3
<211> LENGTH: 93
<212> TYPE: DNA
<213> ORGANISM: Homo sapiens

<400> SEQUENCE: 3
tgagtgcgac cccggtgccc ggtggggaat tttcttggcc tcctggtgga gccttgaatg     60
ccagctcagc ccctcatctc tctcctctgc agg                                  93

<210> SEQ ID NO 4
<211> LENGTH: 31
<212> TYPE: PRT
<213> ORGANISM: Homo sapiens

<400> SEQUENCE: 4
```

-continued

Glu Cys Asp Pro Gly Ala Arg Trp Gly Ile Phe Leu Ala Ser Trp Trp
 1               5                  10                  15

Ser Leu Glu Cys Gln Leu Ser Pro Ser Ser Leu Ser Ser Ala Gly
            20                  25                  30

<210> SEQ ID NO 5
<211> LENGTH: 93
<212> TYPE: DNA
<213> ORGANISM: Homo sapiens

<400> SEQUENCE: 5
tgagtgcgac cccggtgccc ggtggggaat tttcttggcc tctggtggag ccttgaatgc     60
caggctcagc ccctcatctc tcctctctgc agg                                 93

<210> SEQ ID NO 6
<211> LENGTH: 31
<212> TYPE: PRT
<213> ORGANISM: Homo sapiens

<400> SEQUENCE: 6

Glu Cys Asp Pro Gly Ala Arg Trp Gly Ile Phe Leu Ala Ser Gly Gly
 1               5                  10                  15

Ala Leu Asn Ala Arg Leu Ser Pro Ser Ser Leu Ser Ser Ala Gly
            20                  25                  30

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tatgaacttc ctcctgagca ggaa                                           24

<210> SEQ ID NO 8
<211> LENGTH: 1893
<212> TYPE: DNA
<213> ORGANISM: Homo sapiens

<400> SEQUENCE: 8
atgagccgtg agtgcgaccc cggtgcccgg tggggaattt tcttggcctc tggtggagc      60 cttgaatgcc agctcagccc ctcatctctc ctctgcag ggagtctctt gctctggttc      120
ttgctgttcc tgctcctgct cccgccgctc ccgtcctgc tcgcggaccc aggggcgccc     180
acgccagtga atccctgttg ttactatcca tgccagcacc agggcatctg tgtccgcttc     240
ggccttgacc gctaccagtg tgactgcacc cgcacgggct attccggccc caactgcacc     300
atccctggcc tgtggacctg gctccggaat tcactgcggc ccagcccctc tttcacccac     360
ttcctgctca ctcacgggcg ctggttctgg agtttgtca atgccacctt catccgagag     420
atgctcatgc gcctggtact cacagtgcgc tccaacctta tccccagtcc cccaccctac     480
aactcagcac atgactacat cagctgggag tctttctcca acgtgagcta ttacactcgt     540
attctgccct ctgtgcctaa agattgcccc acacccatgg aaccaaagg gaagaagcag     600 ttgccagatg cccagctcct ggcccgccgc ttcctgctca ggaggaagtt catacctgac     660
ccccaaggca ccaacctcat gtttgccttc tttgcacaac acttcaccca ccagttcttc     720
aaaacttctg gcaagatggg tcctggcttc accaaggcct tgggccatgg ggtagacctc     780

```
ggccacattt atgagacaa tctggagcgt cagtatcaac tgcggctctt taaggatggg      840
aaactcaagt accaggtgct ggatggagaa atgtacccgc cctcggtaga agaggcgcct      900
gtgttgatgc actaccccg aggcatcccg ccccagagcc agatggctgt gggccaggag      960
gtgtttgggc tgcttcctgg gctcatgctg tatgccacgc tctggctacg tgagcacaac     1020
cgtgtgtgtg acctgctgaa ggctgagcac cccacctggg gcgatgagca gcttttccag     1080
acgacccgcc tcatcctcat aggggagacc atcaagattg tcatcgagga gtacgtgcag     1140
cagctgagtg gctatttcct gcagctgaaa tttgacccag agctgctgtt cggtgtccag     1200
ttccaatacc gcaaccgcat tgccatggag ttcaaccatc tctaccactg caccccctc     1260
atgcctgact ccttcaaggt gggctcccag gagtacagct acgagcagtt cttgttcaac     1320
acctccatgt tggtggacta tggggttgag gccctggtgg atgccttctc tcgccagatt     1380
gctggccgga tcggtggggg caggaacatg gaccaccaca tcctgcatgt ggctgtggat     1440
gtcatcaggg agtctcggga gatgcggctg cagcccttca atgagtaccg caagaggttt     1500
ggcatgaaac cctacacctc cttccaggag ctcgtaggag agaaggagat ggcagcagag     1560
ttggaggaat tgtatggaga cattgatgcg ttggagttct accctggact gcttcttgaa     1620
aagtgccatc caaactctat ctttgggga agtatgatag agattggggc tccccttttcc     1680
ctcaagggtc tcctagggaa tcccatctgt tctccggagt actggaagcc gagcacattt     1740
ggcggcgagg tgggctttaa cattgtcaag acggccacac tgaagaagct ggtctgcctc     1800
aacaccaaga cctgtcccta cgtttccttc cgtgtgccgg atgccagtca ggatgatggg     1860
cctgctgtgg agcgaccatc cacagagctc tga                                  1893
```

<210> SEQ ID NO 9  
<211> LENGTH: 630  
<212> TYPE: PRT  
<213> ORGANISM: Homo sapiens

<400> SEQUENCE: 9

```
Met Ser Arg Glu Cys Asp Pro Gly Ala Arg Trp Gly Ile Phe Leu Ala
  1               5                  10                  15

Ser Trp Trp Ser Leu Glu Cys Gln Leu Ser Pro Ser Ser Leu Ser Ser
             20                  25                  30

Ala Gly Ser Leu Leu Leu Trp Phe Leu Leu Phe Leu Leu Leu Leu Pro
         35                  40                  45

Pro Leu Pro Val Leu Leu Ala Asp Pro Gly Ala Pro Thr Pro Val Asn
     50                  55                  60

Pro Cys Cys Tyr Tyr Pro Cys Gln His Gln Gly Ile Cys Val Arg Phe
 65                  70                  75                  80

Gly Leu Asp Arg Tyr Gln Cys Asp Cys Thr Arg Thr Gly Tyr Ser Gly
                 85                  90                  95

Pro Asn Cys Thr Ile Pro Gly Leu Trp Thr Trp Leu Arg Asn Ser Leu
            100                 105                 110

Arg Pro Ser Pro Ser Phe Thr His Phe Leu Leu Thr His Gly Arg Trp
        115                 120                 125

Phe Trp Glu Phe Val Asn Ala Thr Phe Ile Arg Glu Met Leu Met Arg
    130                 135                 140

Leu Val Leu Thr Val Arg Ser Asn Leu Ile Pro Ser Pro Pro Thr Tyr
145                 150                 155                 160

Asn Ser Ala His Asp Tyr Ile Ser Trp Glu Ser Phe Ser Asn Val Ser
                165                 170                 175
```

-continued

Tyr Tyr Thr Arg Ile Leu Pro Ser Val Pro Lys Asp Cys Pro Thr Pro
            180                 185                 190

Met Gly Thr Lys Gly Lys Gln Leu Pro Asp Ala Gln Leu Leu Ala
        195                 200                 205

Arg Arg Phe Leu Leu Arg Arg Lys Phe Ile Pro Asp Pro Gln Gly Thr
            210                 215                 220

Asn Leu Met Phe Ala Phe Phe Ala Gln His Phe Thr His Gln Phe Phe
225                 230                 235                 240

Lys Thr Ser Gly Lys Met Gly Pro Gly Phe Thr Lys Ala Leu Gly His
                245                 250                 255

Gly Val Asp Leu Gly His Ile Tyr Gly Asp Asn Leu Glu Arg Gln Tyr
            260                 265                 270

Gln Leu Arg Leu Phe Lys Asp Gly Lys Leu Lys Tyr Gln Val Leu Asp
        275                 280                 285

Gly Glu Met Tyr Pro Pro Ser Val Glu Glu Ala Pro Val Leu Met His
        290                 295                 300

Tyr Pro Arg Gly Ile Pro Pro Gln Ser Gln Met Ala Val Gly Gln Glu
305                 310                 315                 320

Val Phe Gly Leu Leu Pro Gly Leu Met Leu Tyr Ala Thr Leu Trp Leu
            325                 330                 335

Arg Glu His Asn Arg Val Cys Asp Leu Leu Lys Ala Glu His Pro Thr
            340                 345                 350

Trp Gly Asp Glu Gln Leu Phe Gln Thr Thr Arg Leu Ile Leu Ile Gly
        355                 360                 365

Glu Thr Ile Lys Ile Val Ile Glu Glu Tyr Val Gln Gln Leu Ser Gly
        370                 375                 380

Tyr Phe Leu Gln Leu Lys Phe Asp Pro Glu Leu Leu Phe Gly Val Gln
385                 390                 395                 400

Phe Gln Tyr Arg Asn Arg Ile Ala Met Glu Phe Asn His Leu Tyr His
                405                 410                 415

Trp His Pro Leu Met Pro Asp Ser Phe Lys Val Gly Ser Gln Glu Tyr
            420                 425                 430

Ser Tyr Glu Gln Phe Leu Phe Asn Thr Ser Met Leu Val Asp Tyr Gly
        435                 440                 445

Val Glu Ala Leu Val Asp Ala Phe Ser Arg Gln Ile Ala Gly Arg Ile
        450                 455                 460

Gly Gly Gly Arg Asn Met Asp His His Ile Leu His Val Ala Val Asp
465                 470                 475                 480

Val Ile Arg Glu Ser Arg Glu Met Arg Leu Gln Pro Phe Asn Glu Tyr
            485                 490                 495

Arg Lys Arg Phe Gly Met Lys Pro Tyr Thr Ser Phe Gln Glu Leu Val
            500                 505                 510

Gly Glu Lys Glu Met Ala Ala Glu Leu Glu Glu Leu Tyr Gly Asp Ile
        515                 520                 525

Asp Ala Leu Glu Phe Tyr Pro Gly Leu Leu Leu Glu Lys Cys His Pro
        530                 535                 540

Asn Ser Ile Phe Gly Glu Ser Met Ile Glu Ile Gly Ala Pro Phe Ser
545                 550                 555                 560

Leu Lys Gly Leu Leu Gly Asn Pro Ile Cys Ser Pro Glu Tyr Trp Lys
                565                 570                 575

Pro Ser Thr Phe Gly Gly Glu Val Gly Phe Asn Ile Val Lys Thr Ala
            580                 585                 590

```
Thr Leu Lys Lys Leu Val Cys Leu Asn Thr Lys Thr Cys Pro Tyr Val
        595                 600                 605

Ser Phe Arg Val Pro Asp Ala Ser Gln Asp Asp Gly Pro Ala Val Glu
    610                 615                 620

Arg Pro Ser Thr Glu Leu
625                 630

<210> SEQ ID NO 10
<211> LENGTH: 1860
<212> TYPE: DNA
<213> ORGANISM: Homo sapiens

<400> SEQUENCE: 10
atgagccgtg agtgcgaccc cggtgcccgg tggggaattt tcttggcctc tggtggagcc      60
ttgaatgcca ggctcagccc ctcatctctc tcctctgcag ggagtctctt gctctggttc     120
ttgctgttcc tgctcctgct cccgccgctc ccgtcctgc tcgcggaccc aggggcgccc      180
acgccagtga atccctgttg ttactatcca tgccagcacc agggcatctg tgtccgcttc     240
ggccttgacc gctaccagtg tgactgcacc cgcacgggct attccggccc caactgcacc     300
atccctggcc tgtggacctg gctccggaat tcactgcggc ccagcccctc tttcacccac     360
ttcctgctca ctcacgggcg ctggttctgg gagtttgtca atgccacctt catccgagag     420
atgctcatgc gcctggtact cacagtgcgc tccaaccttt ccccagtcc ccccacctac      480 aactcagcac atgactacat cagctggag tctttctcca acgtgagcta ttacactcgt      540
attctgccct ctgtgcctaa agattgcccc acacccatgg aaccaaagg gaagaagcag      600 ttgccagatg cccagctcct ggcccgccgc ttcctgctca ggaggaagtt catacctgac     660
ccccaaggca ccaacctcat gtttgccttc tttcacaac acttcacccca ccagttcttc     720 aaaacttctg caagatgggt cctggcttc accaaggcct gggccatgg ggtagacctc      780 ggccacattt atgagacaaa tctggagcgt cagtatcaac tgcggctctt taaggatggg     840
aaactcaagt accaggtgct ggatggagaa atgtacccgc cctcggtaga agaggcgcct     900
gtgttgatgc actaccccg aggcatcccg cccagagcc agatggctgt gggccaggag      960
gtgtttgggc tgcttcctgg gctcatgctg tatgccacgc tctggctacg tgagcacaac    1020
cgtgtgtgtg acctgctgaa ggctgagcac cccacctggg gcgatgagca gcttttccag    1080
acgacccgcc tcatcctcat aggggagacc atcaagattg tcatcgagga gtacgtgcag    1140
cagctgagtg gctatttcct gcagctgaaa tttgacccag agctgctgtt cggtgtccag    1200
ttccaatacc gcaaccgcat tgccatggag ttcaaccatc tctaccactg cacccctc     1260 atgcctgact ccttcaaggt gggctcccag gagtacagct acgagcagtt cttgttcaac    1320
acctccatgt tggtggacta tgggggttgag gccctggtgg atgccttctc tcgccagatt    1380
gctggccgga tcgtgggggg caggaacatg gaccaccaca cctgcatgt ggctgtggat     1440 gtcatcaggg agtctcggga gatgcggctg cagcccttca atgagtaccg caagaggttt    1500
ggcatgaaac cctacacctc cttccaggag ctcgtaggag agaaggagat ggcagcagag    1560
ttggaggaat tgtatggaga cattgatgcg ttggagttct acctggact gcttcttgaa     1620 aagtgccatc caaactctat cttttgggga gtatgatag agattgggc ccccttttcc      1680 ctcaagggtc tcctagggaa tcccatctgt tctccggagt actggaagcc gagcacattt    1740
ggcggcgagg tgggctttaa cattgtcaag acgccacac tgaagaagct ggtctgcctc     1800
aacaccaaga cctgtcccta cgtttccttc cgtgtgccgg atgccagtca ggatgatggg    1860
```

<210> SEQ ID NO 11
<211> LENGTH: 630
<212> TYPE: PRT
<213> ORGANISM: Homo sapiens

<400> SEQUENCE: 11

```
Met Ser Arg Glu Cys Asp Pro Gly Ala Arg Trp Gly Ile Phe Leu Ala
1               5                   10                  15

Ser Gly Gly Ala Leu Asn Ala Arg Leu Ser Pro Ser Ser Leu Ser Ser
            20                  25                  30

Ala Gly Ser Leu Leu Leu Trp Phe Leu Leu Phe Leu Leu Leu Leu Pro
        35                  40                  45

Pro Leu Pro Val Leu Leu Ala Asp Pro Gly Ala Pro Thr Pro Val Asn
    50                  55                  60

Pro Cys Cys Tyr Tyr Pro Cys Gln His Gln Gly Ile Cys Val Arg Phe
65                  70                  75                  80

Gly Leu Asp Arg Tyr Gln Cys Asp Cys Thr Arg Thr Gly Tyr Ser Gly
                85                  90                  95

Pro Asn Cys Thr Ile Pro Gly Leu Trp Thr Trp Leu Arg Asn Ser Leu
            100                 105                 110

Arg Pro Ser Pro Ser Phe Thr His Phe Leu Leu Thr His Gly Arg Trp
        115                 120                 125

Phe Trp Glu Phe Val Asn Ala Thr Phe Ile Arg Glu Met Leu Met Arg
    130                 135                 140

Leu Val Leu Thr Val Arg Ser Asn Leu Ile Pro Ser Pro Pro Thr Tyr
145                 150                 155                 160

Asn Ser Ala His Asp Tyr Ile Ser Trp Glu Ser Phe Ser Asn Val Ser
                165                 170                 175

Tyr Tyr Thr Arg Ile Leu Pro Ser Val Pro Lys Asp Cys Pro Thr Pro
            180                 185                 190

Met Gly Thr Lys Gly Lys Lys Gln Leu Pro Asp Ala Gln Leu Leu Ala
        195                 200                 205

Arg Arg Phe Leu Leu Arg Arg Lys Phe Ile Pro Asp Pro Gln Gly Thr
    210                 215                 220

Asn Leu Met Phe Ala Phe Phe Ala Gln His Phe Thr His Gln Phe Phe
225                 230                 235                 240

Lys Thr Ser Gly Lys Met Gly Pro Gly Phe Thr Lys Ala Leu Gly His
                245                 250                 255

Gly Val Asp Leu Gly His Ile Tyr Gly Asp Asn Leu Glu Arg Gln Tyr
            260                 265                 270

Gln Leu Arg Leu Phe Lys Asp Gly Lys Leu Lys Tyr Gln Val Leu Asp
        275                 280                 285

Gly Glu Met Tyr Pro Pro Ser Val Glu Glu Ala Pro Val Leu Met His
    290                 295                 300

Tyr Pro Arg Gly Ile Pro Pro Gln Ser Gln Met Ala Val Gly Gln Glu
305                 310                 315                 320

Val Phe Gly Leu Leu Pro Gly Leu Met Leu Tyr Ala Thr Leu Trp Leu
                325                 330                 335

Arg Glu His Asn Arg Val Cys Asp Leu Leu Lys Ala Glu His Pro Thr
            340                 345                 350

Trp Gly Asp Glu Gln Leu Phe Gln Thr Thr Arg Leu Ile Leu Ile Gly
        355                 360                 365

Glu Thr Ile Lys Ile Val Ile Glu Glu Tyr Val Gln Gln Leu Ser Gly
    370                 375                 380
```

-continued

Tyr Phe Leu Gln Leu Lys Phe Asp Pro Glu Leu Leu Phe Gly Val Gln
385                 390                 395                 400

Phe Gln Tyr Arg Asn Arg Ile Ala Met Glu Phe Asn His Leu Tyr His
            405                 410                 415

Trp His Pro Leu Met Pro Asp Ser Phe Lys Val Gly Ser Gln Glu Tyr
            420                 425                 430

Ser Tyr Glu Gln Phe Leu Phe Asn Thr Ser Met Leu Val Asp Tyr Gly
        435                 440                 445

Val Glu Ala Leu Val Asp Ala Phe Ser Arg Gln Ile Ala Gly Arg Ile
    450                 455                 460

Gly Gly Gly Arg Asn Met Asp His His Ile Leu His Val Ala Val Asp
465                 470                 475                 480

Val Ile Arg Glu Ser Arg Glu Met Arg Leu Gln Pro Phe Asn Glu Tyr
                485                 490                 495

Arg Lys Arg Phe Gly Met Lys Pro Tyr Thr Ser Phe Gln Glu Leu Val
                500                 505                 510

Gly Glu Lys Glu Met Ala Ala Glu Leu Glu Glu Leu Tyr Gly Asp Ile
            515                 520                 525

Asp Ala Leu Glu Phe Tyr Pro Gly Leu Leu Leu Glu Lys Cys His Pro
        530                 535                 540

Asn Ser Ile Phe Gly Glu Ser Met Ile Glu Ile Gly Ala Pro Phe Ser
545                 550                 555                 560

Leu Lys Gly Leu Leu Gly Asn Pro Ile Cys Ser Pro Glu Tyr Trp Lys
                565                 570                 575

Pro Ser Thr Phe Gly Gly Glu Val Gly Phe Asn Ile Val Lys Thr Ala
            580                 585                 590

Thr Leu Lys Lys Leu Val Cys Leu Asn Thr Lys Thr Cys Pro Tyr Val
        595                 600                 605

Ser Phe Arg Val Pro Asp Ala Ser Gln Asp Asp Gly Pro Ala Val Glu
    610                 615                 620

Arg Pro Ser Thr Glu Leu
625                 630

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
catatgagcc ggagtctctt gctctggttc                                          30

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtcgactcag agctctgtgg atggtcgctc cac                                      33

<210> SEQ ID NO 14
<211> LENGTH: 38
<212> TYPE: DNA

-continued

<210> SEQ ID NO 14
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tggcattcaa ggctccacca ggaggccaag aaaattcc                           38

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      oligopeptide

<400> SEQUENCE: 15

Met Ser Arg Glu Cys Asp Pro Gly Ala Arg Trp Gly Cys
 1               5                  10

<210> SEQ ID NO 16
<211> LENGTH: 86
<212> TYPE: DNA
<213> ORGANISM: Homo sapiens

<400> SEQUENCE: 16
gagtctcttg ctctggttct tgctgttcct gctcctgctc ccgccgctcc ccgtcctgct    60
cgcggaccca ggggcgccca cgccag                                         86

<210> SEQ ID NO 17
<211> LENGTH: 94
<212> TYPE: DNA
<213> ORGANISM: Homo sapiens

<400> SEQUENCE: 17
tgagtgcgac cccggtgccc ggtgggggaat tttcttggcc tcctggtgga gccttgaatg    60
ccaggctcag cccctcatct ctctcctctg cagg                                94

<210> SEQ ID NO 18
<211> LENGTH: 192
<212> TYPE: DNA
<213> ORGANISM: Homo sapiens
<220> FEATURE:
<221> NAME/KEY: CDS
<222> LOCATION: (1)..(189)

<400> SEQUENCE: 18 atg agc cgt gag tgc gac ccc ggt gcc cgg tgg gga att ttc ttg gcc      48
Met Ser Arg Glu Cys Asp Pro Gly Ala Arg Trp Gly Ile Phe Leu Ala
 1               5                  10                  15 tcc tgg tgg agc ctt gaa tgc cag gct cag ccc ctc atc tct ctc ctc      96
Ser Trp Trp Ser Leu Glu Cys Gln Ala Gln Pro Leu Ile Ser Leu Leu
             20                  25                  30 tgc agg gag tct ctt gct ctg gtt ctt gct gtt cct gct cct gct ccc     144
Cys Arg Glu Ser Leu Ala Leu Val Leu Ala Val Pro Ala Pro Ala Pro
         35                  40                  45 gcc gct ccc cgt cct gct cgc gga ccc agg ggc gcc cac gcc agg tag     192
Ala Ala Pro Arg Pro Ala Arg Gly Pro Arg Gly Ala His Ala Arg
     50                  55                  60

<210> SEQ ID NO 19
<211> LENGTH: 63
<212> TYPE: PRT
<213> ORGANISM: Homo sapiens -continued

<400> SEQUENCE: 19

Met Ser Arg Glu Cys Asp Pro Gly Ala Arg Trp Gly Ile Phe Leu Ala
1               5                   10                  15

Ser Trp Trp Ser Leu Glu Cys Gln Ala Gln Pro Leu Ile Ser Leu Leu
            20                  25                  30

Cys Arg Glu Ser Leu Ala Leu Val Leu Ala Val Pro Ala Pro Ala Pro
        35                  40                  45

Ala Ala Pro Arg Pro Ala Arg Gly Pro Arg Gly Ala His Ala Arg
    50                  55                  60

<210> SEQ ID NO 20
<211> LENGTH: 62
<212> TYPE: PRT
<213> ORGANISM: Homo sapiens

<400> SEQUENCE: 20

Ala Val Ser Ala Thr Pro Val Pro Gly Gly Glu Phe Ser Trp Pro Pro
1               5                   10                  15

Gly Gly Ala Leu Asn Ala Arg Leu Ser Pro Ser Ser Leu Ser Ser Ala
            20                  25                  30

Gly Ser Leu Leu Leu Trp Phe Leu Leu Phe Leu Leu Leu Leu Pro Pro
        35                  40                  45

Leu Pro Val Leu Leu Ala Asp Pro Gly Ala Pro Thr Pro Gly
    50                  55                  60

<210> SEQ ID NO 21
<211> LENGTH: 17
<212> TYPE: PRT
<213> ORGANISM: Homo sapiens

<400> SEQUENCE: 21

Val Arg Pro Arg Cys Pro Val Gly Asn Phe Leu Gly Leu Leu Val Glu
1               5                   10                  15

Pro

<210> SEQ ID NO 22
<211> LENGTH: 42
<212> TYPE: PRT
<213> ORGANISM: Homo sapiens

<400> SEQUENCE: 22

Met Pro Gly Ser Ala Pro His Leu Ser Pro Leu Gln Gly Val Ser Cys
1               5                   10                  15

Ser Gly Ser Cys Cys Ser Cys Ser Cys Ser Arg Arg Ser Pro Ser Cys
            20                  25                  30

Ser Arg Thr Gln Gly Arg Pro Arg Gln Val
        35                  40

<210> SEQ ID NO 23
<211> LENGTH: 189
<212> TYPE: DNA
<213> ORGANISM: Homo sapiens
<220> FEATURE:
<221> NAME/KEY: CDS
<222> LOCATION: (1)..(189)

<400> SEQUENCE: 23 atg agc cgt gag tgc gac ccc ggt gcc cgg tgg gga att ttc ttg gcc      48
Met Ser Arg Glu Cys Asp Pro Gly Ala Arg Trp Gly Ile Phe Leu Ala
1               5                   10                  15

```
tcc tgg tgg agc ctt gaa tgc cag ctc agc ccc tca tct ctc tcc tct      96
Ser Trp Trp Ser Leu Glu Cys Gln Leu Ser Pro Ser Ser Leu Ser Ser
         20                  25                  30 gca ggg agt ctc ttg ctc tgg ttc ttg ctg ttc ctg ctc ctg ctc ccg     144
Ala Gly Ser Leu Leu Leu Trp Phe Leu Leu Phe Leu Leu Leu Leu Pro
         35                  40                  45 ccg ctc ccc gtc ctg ctc gcg gac cca ggg gcg ccc acg cca ggt         189
Pro Leu Pro Val Leu Leu Ala Asp Pro Gly Ala Pro Thr Pro Gly
 50                  55                  60
```

<210> SEQ ID NO 24
<211> LENGTH: 63
<212> TYPE: PRT
<213> ORGANISM: Homo sapiens

<400> SEQUENCE: 24

Met Ser Arg Glu Cys Asp Pro Gly Ala Arg Trp Gly Ile Phe Leu Ala
 1               5                  10                  15

Ser Trp Trp Ser Leu Glu Cys Gln Leu Ser Pro Ser Ser Leu Ser Ser
                20                  25                  30

Ala Gly Ser Leu Leu Leu Trp Phe Leu Leu Phe Leu Leu Leu Leu Pro
         35                  40                  45

Pro Leu Pro Val Leu Leu Ala Asp Pro Gly Ala Pro Thr Pro Gly
 50                  55                  60

<210> SEQ ID NO 25
<211> LENGTH: 180
<212> TYPE: DNA
<213> ORGANISM: Homo sapiens
<220> FEATURE:
<221> NAME/KEY: CDS
<222> LOCATION: (1)..(180)

<400> SEQUENCE: 25

```
atg agc cgt gag tgc gac ccc ggt gcc cgg tgg gga att ttc ttg gcc      48
Met Ser Arg Glu Cys Asp Pro Gly Ala Arg Trp Gly Ile Phe Leu Ala
 1               5                  10                  15 tct ggt gga gcc ttg aat gcc agg ctc agc ccc tca tct ctc tcc tct     96
Ser Gly Gly Ala Leu Asn Ala Arg Leu Ser Pro Ser Ser Leu Ser Ser
         20                  25                  30 gca ggg agt ctc ttg ctc tgg ttc ttg ctg ttc ctg ctc ctg ctc ccg     144
Ala Gly Ser Leu Leu Leu Trp Phe Leu Leu Phe Leu Leu Leu Leu Pro
         35                  40                  45 ccg ctc ccc gtc ctg ctc gcg gac cca ggg gcg ccc                     180
Pro Leu Pro Val Leu Leu Ala Asp Pro Gly Ala Pro
 50                  55                  60
```

<210> SEQ ID NO 26
<211> LENGTH: 60
<212> TYPE: PRT
<213> ORGANISM: Homo sapiens

<400> SEQUENCE: 26

Met Ser Arg Glu Cys Asp Pro Gly Ala Arg Trp Gly Ile Phe Leu Ala
 1               5                  10                  15

Ser Gly Gly Ala Leu Asn Ala Arg Leu Ser Pro Ser Ser Leu Ser Ser
                20                  25                  30

Ala Gly Ser Leu Leu Leu Trp Phe Leu Leu Phe Leu Leu Leu Leu Pro
         35                  40                  45

Pro Leu Pro Val Leu Leu Ala Asp Pro Gly Ala Pro
 50                  55                  60

```
<210> SEQ ID NO 27
<211> LENGTH: 32
<212> TYPE: PRT
<213> ORGANISM: Unknown Organism
<220> FEATURE:
<223> OTHER INFORMATION: Description of Unknown Organism: Canine
      sequence

<400> SEQUENCE: 27

Glu Phe Asp Pro Glu Ala Pro Arg Asn Pro Leu Arg Leu Pro Gly Glu
 1               5                  10                  15

Pro Arg Met Pro Gly Pro Ala Leu Thr Ser Arg Ser Ala Gly Gly Ser
            20                  25                  30
```

HUMAN CYCLOOXYGENASE-3 ENZYME AND USES THEREOF

CROSS-REFERENCE TO RELATED APPLICATIONS

This application is a continuation of U.S. patent application Ser. No. 10/783,297 filed Feb. 20, 2004, now abandoned, which claims benefit of U.S. Provisional Application No. 60/449,230, filed Feb. 21, 2003, all of which are hereby incorporated by reference in their entireties.

FIELD OF THE INVENTION

The present invention relates to a cyclooxygenase isozyme. In particular, the present invention relates to isolated nucleic acid molecules and polypeptides of a novel human cyclooxygenase isozyme COX-3 and uses thereof. This case claims priority from U.S. Provisional Application No. 60/449,230 filed Feb. 21, 2003 and entitled, "Human Cyclooxygenase-3 Enzyme and Uses Thereof" which is hereby incorporated by reference in its entirety.

BACKGROUND OF THE INVENTION

Non-steroidal anti-inflammatory drugs (NSAIDs) have been used in various forms for more than 3,500 years. This class of anti-inflammatory agents exerts anti-inflammatory, analgesic and antipyretic actions. Examples of NSAIDs include, but are not limited to, aspirin, ibuprofen, ketoprofen, piroxicam, naproxen, sulindac, choline subsalicylate, diflunisal, fenoprofen, indomethacin, meclofenamate, salsalate, tolmetin, and magnesium salicylate. It is believed that NSAIDs work by inhibiting the production of prostaglandins (PGs), a group of compounds derived from unsaturated 20-carbon fatty acids, primarily arachidonic acid, via the cyclooxygenase (COX) pathway.

At sites of inflammation, COX converts arachidonic acid into the endoperoxide $PGG_2$, which then breaks down to prostaglandin $H_2$ ($PGH_2$). $PGH_2$ in turn is converted into prostanoids including $PGD_2$, $PGE_2$, $PGF_{2\alpha}$, $PGI_2$, and thromboxane $A_2$ ($TxA_2$). The local production of prostanoids, such as $PGE_2$, can sensitize pain nerve endings and increase blood flow, promoting feelings of pain and driving tissue swelling and redness.

NSAIDs selectively inhibit COX activity, thereby inhibiting $PGE_2$ formation and minimizing inflammation (Warner et al., 2002, *Proc. Natl. Acad. Sci. USA*, 99:13371-13373). Unfortunately, the use of NSAIDs is often limited by side effects, such as gastrointestinal bleeding, ulcers, renal failure, and others. These side effects are caused by the undesirable reduction of prostaglandins in general. Prostaglandins can function as autocrine and paracrine stimulants in normal cells for the maintenance of normal physiology. The development of new agents that will act more specifically by achieving a reduction in prostaglandins in target cells without altering prostaglandin production in normal cells is one of the major goals of NSAID research.

Acetaminophen, is a safe and effective analgesic for the relief of mild to moderate pain associated with oral surgery, episiotomy, postpartum pain, cancer, osteoarthritis, headache, dysmenorrhea, and the like. Unlike NSAIDs such as aspirin, acetaminophen possesses potent antipyretic and analgesic actions (Botting, 2000, *Clin. Infect. Diseases*. 31:S202-10). Clinical trials have demonstrated that acetaminophen lacks the gastrointestinal side effects of aspirin. Further, acetaminophen has no effect on the hemostatic mechanism in children and can be used in clinical situations where the use of aspirin may cause dangerous bleeding. In spite of its wide use, the mechanism of action of acetaminophen has not been fully elucidated.

Until very recently, only two isoforms of cyclooxygenase had been identified: COX-1, which is constitutively expressed, and COX-2, which is inducible. COX-1 appears to be responsible for the production of physiologically relevant prostanoids, such as the $PGI_2$ and $PGE_2$ in the gastrointestinal (GI) tract whereby they are protective to the stomach. Cox-1 is also involved in the production of $TxA_2$, a potent inducer of platelet aggregation and causes vasoconstriction. In addition to their role in anti-inflammation, inhibitors of COX-1, such as aspirin, inhibit blood coaglutation, and are associated with GI toxicity. COX-2 is rapidly up-regulated at inflammatory sites and appears to be responsible for the formation of proinflammatory prostanoids. The more selective COX-2 inhibitors would likely have reduced GI toxicity, but would still relieve pain and other classic signs of inflammation, such as heat, redness, and swelling. Neither COX-1 nor COX-2 are sensitive to acetaminophen at therapeutic concentrations of the drug when assayed in whole cells or cell homogenates, suggesting that neither COX-1 nor COX-2 are good targets for the action of acetaminophen.

A gene encoding the third cyclooxygenase isozyme or COX-3 has been recently identified from canine cerebral cortex (Chandrasekharan et al., 2002, *Proc. Natl. Acad. Sci. USA*, 99:13926-31). The inhibition of COX-3 was suggested to represent a primary central mechanism for the action of acetaminophen. The dog COX-3 gene is a splicing variant of the dog COX-1 gene with retention of intron 1. The dog COX-3 protein contains an amino acid sequence identical to that of the dog COX-1 protein at the carboxyl terminus and an insertion of 33 amino acids at the amino terminus. The dog COX-3 mRNA is expressed in canine cerebral cortex and in lesser amounts in other tissues analyzed. Functional studies have demonstrated that the dog COX-3 possesses glycosylation-dependent cyclooxygenase activity, and is potently inhibited by some, but not all, NSAIDs. A comparison of dog COX-3 activity with murine COX-1 and -2 demonstrates that dog COX-3 is selectively inhibited by analgesic/antipyretic drugs such as acetaminophen, phenacetin, antipyrine, and dipyrone. For example, at a substrate concentration of 5 mM, acetaminophen is 100-fold selective for inhibition of dog COX-3 versus murine COX-2 and 2-fold selective versus murine COX-1 (Chandrasekharan et al., 2002, supra).

Although dog COX-3 has been identified from canine cerebral cortex, the existence of human COX-3 required further experimentation because based on the published human genome sequences, intron 1 of human COX-1 is out of frame with the rest of the coding sequence of human COX-1. It was not known whether the published human genome sequences constitute genuine polymorphisms or sequencing errors (Chandrasekharan et al., 2002, supra). Carefully designed studies need to be performed in order to demonstrate the existence of human COX-3 or lack thereof. Results from human COX-3 studies can be useful in elucidating the mechanism of existing analgesics, such as acetaminophen, and to develop more specific analgesics with fewer side effects.

SUMMARY OF THE INVENTION

The present invention relates to isolated nucleic acid molecules encoding a novel human cyclooxygenase isozyme, herein referred to as human COX-3, the polypeptides encoded by the isolated nucleic acid sequences, and the use of the nucleic acid molecules and polypeptides thereof.

Other aspects, features and advantages of the invention will be apparent from the following disclosure, including the detailed description of the invention and its preferred embodiments and the appended claims.

BRIEF DESCRIPTION OF THE DRAWINGS

FIG. 1A shows the DNA sequences of exon 1, intron 1, (SEQ ID NO: 17), and exon 2 (SEQ ID NO: 16) of human Cox-2, as published in the NCBI human genomic database.

FIG. 1B shows that none of the three reading frames (a, b, and c) results in a polypeptide that comprises the amino acid sequences encoded by exon 1, intron 1, and exon 2. A termination of translation is indicated by a *. The nucleotide sequences of exon 1 and exon 2, and their encoded amino acid sequences as in Cox1 are shaded. The figure discloses SEQ ID NO: 18 coding SEQ ID NOS: 19-22, respectively, in order of appearance.

FIG. 1C shows translation of Cox-3a after RNA editing (SEQ ID NO: 23 coding SEQ ID NO: 24).

FIG. 1D shows translation of Cox-3b after RNA editing (SEQ ID NO: 25 coding SEQ ID NO: 26).

FIG. 1E shows a comparison of peptide sequences encoded by COX-1 intron 1 in human and canine COX-3 with (human) or without (canine) RNA editing (SEQ ID NOS: 27, 4, and 6, respectively, in order of appearance). The alignment was performed using the algorithm of Needleman and Wunsch to find the alignment of two complete sequences. The alignment maximizes the number of matches and minimizes the number of gaps. Match display thresholds for the alignment(s): |=IDENTITY; :=2; .=1.

DETAILED DESCRIPTION OF THE INVENTION

Figure 2:
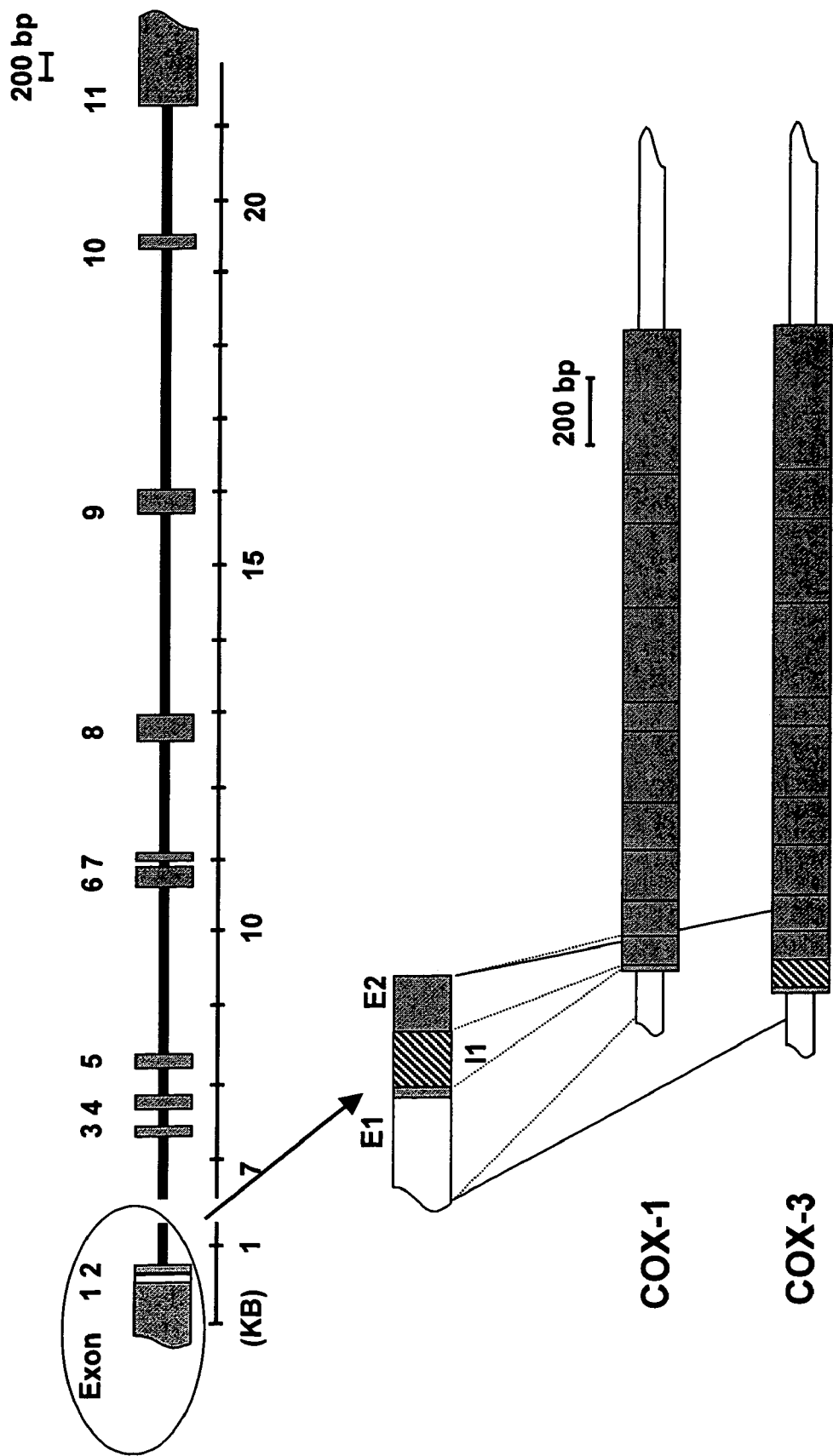
FIG. 2 illustrates gene structure of human COX-3 and COX-1.

All publications cited in this specification are hereby incorporated by reference. Unless defined otherwise, all technical and scientific terms used herein have the same meaning as commonly understood to one of ordinary skill in the art to which this invention pertains.

The terms "including," "comprising", "containing", and "having" are used herein in their open, non-limiting sense.

The following are abbreviations that are at times used in this specification:
bp=base pair
cDNA=complementary DNA
CNS=central nervous system
COX=cyclooxygenase
kb=kilobase; 1000 base pairs
kDa=kilodalton; 1000 dalton
NSAIDs=Non-steroidal anti-inflammatory drugs
nt=nucleotide
PAGE=polyacrylamide gel electrophoresis
PCR=polymerase chain reaction
PG=prostaglandin
SDS=sodium dodecyl sulfate
SiRNA=small interfering RNA
UTR=untranslated region An "activity", a "biological activity", or a "functional activity" of a polypeptide or nucleic acid of the invention refers to an activity exerted by a polypeptide or nucleic acid molecule of the invention as determined in vivo or in vitro, according to standard techniques. Such activities can be a direct activity, such as an association with or an enzymatic activity on a second protein, or an indirect activity, such as a cellular signaling activity mediated by interaction of the protein with a second protein. An exemplary biological activity associated with human COX-3 is its enzymatic activity to convert arachidonic acid to $PGH_2$, and this activity is selectively inhibited by analgesic/antipyretic drugs, such as acetaminophen.

An "analgesic" or "analgesic drug" is an agent that alleviates pain without causing loss of consciousness. An "antipyretic" or "antipyretic drug" is an agent that relieves or reduces fever. An "antipyretic" is the synonym of antifebrile, antithermic, or febrifuge. An "anti-inflammatory drug" is an agent that counteract or suppressing inflammation. An "analgesic/antipyretic drug" is an agent that has both the "analgesic" and "antipyretic" activity.

An "antibody" as used herein refers to an immunoglobulin molecule and immunologically active portions of an immunoglobulin molecule, i.e., a molecule that contains an antigen binding site which specifically binds an antigen, such as a polypeptide of the invention, e.g., an epitope of a polypeptide of the invention. A molecule that specifically binds to a given polypeptide of the invention is a molecule that binds the polypeptide, but does not substantially bind different types of molecules in a sample, e.g., a biological sample, which naturally contains the polypeptide. Examples of immunologically active portions of immunoglobulin molecules include Fab and $F(ab)'_2$ fragments which can be generated by treating the antibody with an enzyme such as pepsin.

An "antibody" can be a monoclonal antibody or a polyclonal antibody. The term "monoclonal antibody" or "monoclonal antibody composition" refers to a population of antibody molecules that contain only one species of an antigen binding site capable of immunoreacting with a particular epitope. The term "polyclonal antibody" refers to antibodies directed against a polypeptide or polypeptides of the invention capable of immunoreacting with more than one epitopes. Particularly preferred polyclonal antibody preparations are ones that contain only antibodies directed against a polypeptide or polypeptides of the invention.

An "antigen" as used herein refers to a molecule containing one or more epitopes that will stimulate a host's immune system to make a humoral and/or cellular antigen-specific response. The term is also used herein interchangeably with "immunogen." The term "epitope" as used herein refers to the site on an antigen or hapten to which a specific antibody molecule binds. The term is also used herein interchangeably with "antigenic determinant" or "antigenic determinant site."

The term "biological sample" refers to a sample obtained from an organism (e.g., patient) or from components (e.g., cells) of an organism. The sample may be of any biological tissue, cell(s) or fluid. The sample may be a "clinical sample" which is a sample derived from a patient. Such samples include, but are not limited to, sputum, blood, blood cells (e.g., white cells), amniotic fluid, plasma, semen, bone marrow, and tissue or fine needle biopsy samples, urine, peritoneal fluid, and pleural fluid, or cells therefrom. Biological samples may also include sections of tissues such as frozen sections taken for histological purposes. A biological sample may also be referred to as a "patient sample." A "biological sample" may also include a substantially purified or isolated protein, membrane preparation, or cell culture.

A "clone" is a population of cells derived from a single cell or common ancestor by mitosis. A "cell line" is a clone of a primary cell that is capable of stable growth in vitro for many generations.

The term "cyclooxygenase", "cyclooxygenase enzyme", "COX", or "COX enzyme", also termed "prostaglandin endoperoxide H synthase" or "PGHS" is an enzyme present in most tissues that catalyses two steps in prostaglandin biosynthesis and produces prostaglandins and thromboxanes from arachidonic acid. The cyclooxygenase catalyzes both the oxidation of arachidonic acid to the hydroperoxide prostaglandin $G_2$ (cyclooxygenase reaction) and its subsequent reduction (peroxidase reaction) to prostaglandin $H_2$ ($PGH_2$). $PGH_2$ is a common intermediate for subsequent isomerisation or cyclization to prostanoids including $PGD_2$, $PGE_2$, $PGF_{2\alpha}$, $PGI_2$, and thromboxane $A_2$ (TxA2). NSAIDs inhibit the cyclooxygenase activity, accounting for their anti-inflammatory effects.

A "disorder related to a COX-3 activity" shall include a disorder or disease associated with over-activity or insufficient activity of a COX-3 enzyme, and conditions that accompany this disorder or disease. "Overactivity of a COX-3 enzyme" refers to either 1) COX-3 expression in cells which normally do not express COX-3; 2) increased COX-3 expression; 3) increased activity of COX-3 per unit of the COX-3 enzyme; or 4) mutations leading to constitutive activation of one or more COX-3 biological activities. "Insufficient activity of COX-3 enzyme" refers to either 1) the absence of COX-3 expression in cells which normally express COX-3; 2) decreased COX-3 expression; 3) decreased activity of COX-3 per unit of the COX-3 enzyme; or 4) mutations leading to constitutive inactivation of one or more COX-3 biological activities.

A "gene" is a segment of DNA involved in producing a peptide, polypeptide, or protein, including the coding region, non-coding regions preceding ("5'UTR") and following ("3'UTR") coding region. A "gene" may also include intervening non-coding sequences ("introns") between individual coding segments ("exons"). "Promoter" means a regulatory sequence of DNA that is involved in the binding of RNA polymerase to initiate transcription of a gene. Promoters are often upstream ("5' to") the transcription initiation site of the gene. A "regulatory sequence" refers to the portion of a gene that can control the expression of the gene. A "regulatory sequence" can include promoters, enhancers and other expression control elements such as polyadenylation signals, ribosome binding site (for bacterial expression), and/or, an operator. A "coding region" refers to the portion of a gene that encodes for amino acids and the start and stop signals for the translation via triplet-base codens.

"Gene therapy" means the introduction of a functional gene, genes, or a nucleic acid fragment from some source by any suitable means into a living cell to correct for a genetic defect.

"Genetic variant" or "variant" means a specific allele which is present at a particular genetic locus in at least one individual in a population and that differs from the wild type allele. "Wild type allele" means the most frequently encountered allele of a given nucleotide sequence in a population.

A "host cell" refers to a cell that contains a DNA molecule of the invention either on a vector or integrated into a cell chromosome. A "host cell" can be either an endogenous host cell that expresses a DNA molecule of the invention endogenously, or a recombinant host cell.

"Human cyclooxygenase-3", "human COX-3", or "hCOX-3" as used herein, refers to a novel member of the cyclooxygenase enzyme that is capable of converting arachidonic acid to the prostaglandin precursor prostaglandin $H_2$, and comprises an amino acid sequence that has greater than about 60% amino acid sequence identity to SEQ ID NO:4 or SEQ ID NO:6. Examples of hCOX-3 include a novel member of the cyclooxygenase enzyme that is capable of converting arachidonic acid to the prostaglandin precursor prostaglandin $H_2$, and comprises an amino acid sequence that has greater than about 60, 65, 70, 75, 80, 85, 90, or 95% amino acid sequence identity to SEQ ID NO:4 or SEQ ID NO:6. In one embodiment, the hCOX-3 comprises SEQ ID NO:9. In another embodiment, the hCox-3 comprises SEQ ID NO:11.

A fragment, or physical association of fragments can have the biological activity associated with the full-length hCOX-3, however, the degree of hCOX-3 activity associated with individual hCOX-3 fragments can vary. An "active fragment of human cyclooxygenase-3" refers to a fragment of human cyclooxygenase-3 that is still capable of converting arachidonic acid to the prostaglandin precursor prostaglandin $H_2$. Examples of "active fragment of human cyclooxygenase-3" can comprise an amino acid sequence that has greater than about 90 or 95% amino acid sequence identity, to the sequence of at least five consecutive amino acids of SEQ ID NO:4 or SEQ ID NO:6, and such an active fragment of hCOX-3 is still capable of converting arachidonic acid to the prostaglandin precursor prostaglandin $H_2$.

The term "inflammation" refers to a localized protective response elicited by injury or destruction of tissues, which serves to destroy, dilute or wall off (sequester) both the injurious agent and the injured tissue. "Inflammation" is characterized in the acute form by the classical signs of pain (dolor), heat (calor), redness (rubor), swelling (tumour) and loss of function (functio laesa). Histologically, inflammation involves a complex series of events, including dilatation of arterioles, capillaries and venules, with increased permeability and blood flow, exudation of fluids, including plasma proteins and leucocytic migration into the inflammatory focus.

An "isolated" nucleic acid molecule is one that is separated from other nucleic acid molecules. An "isolated" nucleic acid molecule can be, for example, a nucleic acid molecule that is free of at least one of the nucleotide sequences that naturally flank the nucleic acid molecule at its 5' and 3' ends in the genomic DNA of the organism from which the nucleic acid is derived. An isolated nucleic acid molecule includes, without limitation, a separate nucleic acid molecule (e.g., a cDNA or genomic DNA fragment produced by PCR or restriction endonuclease treatment) independent of other sequences, as well as a nucleic acid molecule that is incorporated into a vector, an autonomously replicating plasmid, a virus (e.g., a retrovirus, adenovirus, or herpes virus), or into the genomic DNA of a prokaryote or eukaryote. In addition, an isolated nucleic acid molecule can include a nucleic acid molecule that is part of a hybrid or fusion nucleic acid molecule. An isolated nucleic acid molecule can be a nucleic acid sequence that is: (i) amplified in vitro by, for example, polymerase chain reaction (PCR); (ii) synthesized by, for example, chemical synthesis; (iii) recombinantly produced by cloning; or (iv) purified, as by cleavage and electrophoretic or chromatographic separation.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cell from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest. Isolated biologically active polypeptide can have several different physical forms. The isolated polypeptide can exist as a full-length nascent or unprocessed polypeptide, or as partially processed polypeptides or combinations of processed polypeptides. An isolated or substantially purified polypeptide can be a polypeptide encoded by an isolated nucleic acid sequence, as well as polypeptides synthesized by, for example, chemical synthetic methods, and polypeptides separated from biological materials, and then purified, using conventional protein analytical or preparatory procedures, to an extent that permits them to be used according to the methods described herein.

"Nucleic acid" as used herein, refers to a molecule comprised of one or more nucleotides, i.e., ribonucleotides, deoxyribonucleotides, or both. The term includes monomers and polymers of ribonucleotides and deoxyribonucleotides, with the ribonucleotides and/or deoxyribonucleotides being bound together, in the case of the polymers, via 5' to 3' linkages. The ribonucleotide and deoxyribonucleotide polymers may be single or double-stranded. However, linkages may include any of the linkages known in the art including, for example, nucleic acids comprising 5' to 3' linkages. The nucleotides may be naturally occurring or may be synthetically produced analogs that are capable of forming base-pair relationships with naturally occurring base pairs. Examples of naturally occurring base pairs are thymidine, adenine, cytosine, guanine, an uracil; abbreviated T, A, C, G, and U, respectively. Examples of non-naturally occurring bases that are capable of forming base-pairing relationships include, but are not limited to, aza and deaza pyrimidine analogs, aza and deaza-purine analogs, and other heterocyclic base analogs, wherein one or more of the carbon and nitrogen atoms of the pyrimidine rings have been substituted by heteroatoms, e.g., oxygen, sulfur, selenium, phosphorus, and the like. Furthermore, the term "nucleic acid sequences" contemplates the complementary sequence and specifically includes any nucleic acid sequence that is substantially homologous to both the nucleic acid sequence and its complement.

The term "oligonucleotide" refers to a single stranded DNA or RNA sequence of a relatively short length, for example, less than 100 residues long. For many methods, oligonucleotides of about 16-25 nucleotides in length are useful, although longer oligonucleotides of greater than about 25 nucleotides may sometimes be utilized. Some oligonucleotides can be used as "primers" for the synthesis of complimentary nucleic acid strands. For example, DNA primers can hybridize to a complimentary sequence to prime the synthesis of a complimentary DNA strand in reactions using DNA polymerases. Oligonucleotides are also useful for hybridization for nucleic acid detection, for example, in Northern blotting.

"Polymorphism" refers to a set of genetic variants at a particular genetic locus among individuals in a population.

A "polynucleotide" refers to a linear polymer of at least two nucleotides joined together by phosphodiester bonds and may comprise either ribonucleotides or deoxyribonucleotides.

A "polypeptide" or "protein" refers to the arrangement of amino acid residues in a polymer. Polypeptide can be composed of the standard 20 naturally occurring amino acids, in addition to rare amino acids and synthetic amino acid analogs. Shorter polypeptides are generally referred to as peptides. A "recombinant polypeptide" refers to a polypeptide produced by recombinant DNA techniques; i.e., produced from cells transformed by an exogenous DNA construct encoding the desired polypeptide. A "synthetic polypeptide" refers to that prepared by chemical synthesis.

"Promoter" means a regulatory sequence of DNA that is involved in the binding of RNA polymerase to initiate transcription of a gene. Promoters are often upstream ("5' to") the transcription initiation site of the gene.

"Prostanoids" is a collective term for prostaglandins, prostacyclins and thromboxanes. It includes a group of compounds derived from unsaturated 20-carbon fatty acids, primarily arachidonic acid, via the cyclooxygenase pathway. They are extremely potent mediators of a diverse group of physiological processes, including inflammation. Examples of prostanoids include, but are not limited to, $PGD_2$, $PGE_2$, $PGF_{2\alpha}$, $PGI_2$, and thromboxane $A_2$ ($TxA_2$).

"Recombinant" refers to nucleic acid, a protein encoded by a nucleic acid, a cell, or a viral particle, that has been modified using molecular biology techniques to something other than its natural state. For example, recombinant cells can contain nucleotide sequence that is not found within the native (non-recombinant) form of the cell or can express native genes that are otherwise abnormally expressed, under expressed, or not expressed at all. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained, for example, by gene replacement, and site-specific mutation.

A "recombinant host cell" is a cell containing a recombinant DNA sequence. Recombinant DNA sequence can be introduced into host cells using any suitable method including, for example, electroporation, calcium phosphate precipitation, microinjection, transformation, biolistics and viral infection. Recombinant DNA may or may not be integrated (covalently linked) into chromosomal DNA making up the genome of the cell. For example, the recombinant DNA can be maintained on an episomal element, such as a plasmid. Alternatively, with respect to a stably transformed or transfected cell, the recombinant DNA has become integrated into the chromosome so that it is inherited by daughter cells through chromosome replication. This stability is demonstrated by the ability of the stably transformed or transfected cell to establish cell lines or clones comprised of a population of daughter cells containing the exogenous DNA. Recombinant host cells may be prokaryotic or eukaryotic, including bacteria such as *E. coli*, fungal cells such as yeast, mammalian cells such as cell lines of human, bovine, porcine, monkey and rodent origin, and insect cells such as *Drosophila* and silkworm derived cell lines. It is further understood that the term "recombinant host cell" refers not only to a particular cell, but also to the progeny or potential progeny of such a cell. Because certain modifications can occur in succeeding generations due to either mutation or environmental influences, such progeny may not, in fact, be identical to the parent cell, but are still included within the scope of the term as used herein.

"Sequence" means the linear order in which monomers occur in a polymer, for example, the order of amino acids in a polypeptide or the order of nucleotides in a polynucleotide.

"Sequence identity or similarity", as known in the art, is the relationship between two or more polypeptide sequences or two or more polynucleotide sequences, as determined by comparing the sequences. In the art, identity also means the degree of sequence relatedness between polypeptide or polynucleotide sequences, as the case can be as determined by the match between strings of such sequences. To determine the percent identity or similarity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same or similar amino acid residue or nucleotide as the corresponding position in the second sequence, then the molecules are identical or similar at that position. The percent identity or similarity between the two sequences is a function of the number of identical or similar positions shared by the sequences (i.e., % identity=# of identical positions/total # of positions (e.g., overlapping positions)×100). In one embodiment, the two sequences are the same length.

Both identity and similarity can be readily calculated. Methods commonly employed to determine identity or similarity between sequences include, but are not limited to those disclosed in Carillo et al, (1988.), *SIAM J. Applied Math.* 48, 1073. Preferred methods to determine identity are designed to give the largest match between the sequences tested. Methods to determine identity and similarity are codified in computer programs.

A non-limiting example of a mathematical algorithm utilized for the comparison of two sequences is the algorithm of Karlin et al., (1990), *Proc. Natl. Acad. Sci. USA* 87:2264-2268, modified as in Karlin et al., (1993), *Proc. Natl. Acad. Sci. USA* 90:5873-5877. Such an algorithm is incorporated into the NBLAST and XBLAST programs of Altschul et al., (1990), *J Mol. Biol* 215:403-410. To obtain gapped alignments for comparison purposes, Gapped BLAST can be utilized as described in Altschul et al., (1997), *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. Additionally, the FASTA method (Atschul et al., (1990), *J. Molec. Biol.* 215, 403), can also be used.

Another non-limiting example of a mathematical algorithm useful for the comparison of sequences is the algorithm of Myers et al, (1988), *CABIOS* 4:11-17. Such an algorithm is incorporated into the ALIGN program (version 2.0).

In a preferred embodiment, the percent identity between two sequences is determined using the Needleman and Wunsch (*J. Mol. Biol.* (48):444-453 (1970)) algorithm which has been incorporated into the GAP program in the GCG software package. The GCG GAP program aligns two complete sequences to maximize the number of matches and minimizes the number of gaps.

In another preferred embodiment, the percent identity between two sequences is determined using the local homology algorithm of Smith and Waterman (*J Mol Biol.* 1981, 147(1):195-7), which has been incorporated into the BestFit program in the GCG software package. The BestFit program makes an optimal alignment of the best segment of similarity between two sequences. Optimal alignments are found by inserting gaps to maximize the number of matches.

Hybridization can also be used as a test to indicate that two polynucleotides are substantially identical to each other. Polynucleotides that share a sufficient degree of identity will hybridize to each other under stringent hybridization conditions. "Stringent hybridization conditions" has the meaning known in the art, as described in Sambrook et al., *Molecular Cloning: A Laboratory Manual*, Second Edition, Cold Spring Harbor Laboratory, Cold Spring Harbor, N.Y., (1989). An exemplary stringent hybridization condition comprising hybridization in 6× sodium chloride/sodium citrate (SSC) at about 45° C., followed by one or more washes in 0.2×SSC and 0.1% SDS at 50-65° C.

"Substantially similar" as used herein, includes identical sequences, as well as deletions, substitutions or additions to a polynucleotide or polypeptide sequence that maintains any biologically active portion and possesses any of the conserved motifs thereof.

A "subject" as used herein, refers to an animal, preferably a mammal, most preferably a human, who has been the object of treatment, observation or experiment.

A "tag" as used herein refers to an amino acid sequence or a nucleotide sequence that encodes an amino acid sequence that facilitates isolation, purification or detection of a protein containing the tag. A wide variety of such tags are known to those skilled in the art and are suitable for use in the present invention. Suitable tags include, but are not limited to, HA peptide, polyhistidine peptides, biotin/avidin, and a variety of antibody epitope binding sites.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. Methods are known in the art for determining therapeutically effective doses for the instant pharmaceutical composition.

A "vector" refers to a nucleic acid molecule capable of transporting another nucleic acid to which it has been linked. One type of vector is a "plasmid", which refers to a circular double stranded DNA loop into which additional DNA segments can be inserted. Another type of vector is a viral vector, wherein additional DNA segments can be inserted. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, vectors useful for recombinant DNA techniques are often in the form of plasmids. However, the invention is intended to include such other forms of vectors, such as viral vectors (e.g., replication defective retroviruses, adenoviruses and adeno-associated viruses), which serve equivalent functions.

Isolated Nucleic Acid Molecule of the Invention

The present invention demonstrated for the first time the existence of a human COX-3 gene, which is formed via one or more than one RNA editing events following the retention of intron 1 between exon 1 and exon 2 of the human COX-1 gene. The human COX-3a protein (SEQ ID NO:9) comprises the amino acid sequence encoded by exon 1 of human COX- 1, an insertion of 31 amino acids (SEQ ID NO: 4) encoded by intron 1 of human COX-1 after RNA editing (SEQ ID NO: 3), and the amino acid sequence encoded by exon 2 to 11 of human COX-1. The human COX-3b protein (SEQ ID NO:11) comprises the amino acid sequence encoded by exon 1 of human COX-1, an insertion of 31 amino acids (SEQ ID NO: 6) encoded by intron 1 of human COX-1 after RNA editing at a different site (SEQ ID NO: 5), and the amino acid sequence encoded by exon 2 to 11 of human COX-1. The cloning of human Cox-1 was described previously (Yokoyama et al., (1989), *Biochem Biophys Res Commun*, 165(2):888-94). The GenBank accession number for the cDNA or protein of human COX-1 is NM_000962 or NP_000953, respectively. A comparison of the gene structures of human COX-3 and COX-1 is illustrated in FIG. 2.

One aspect of the invention pertains to isolated nucleic acid molecules that encode a human COX-3 or a biologically active portion thereof, as well as nucleic acid molecules of at least 12 sequential nucleotides in length for use as hybridization probes or PCR primers, to identify or amplify nucleic acid molecules encoding a human COX-3 polypeptide of the invention.

In one embodiment, the invention provides an isolated nucleic acid molecule comprising a nucleotide sequence encoding a member of the cyclooxygenase enzyme that is capable of converting arachidonic acid to the prostaglandin precursor prostaglandin H2, and comprises an amino acid sequence that has greater than about 60% amino acid sequence identity, preferably about 65, 70, 75, 80, 85, 90, or 95% amino acid sequence identity, to SEQ ID NO:4 or SEQ ID NO:6, or a complement thereof. A nucleic acid molecule which is a complement of a given nucleotide sequence is one which is sufficiently complementary to the given nucleotide sequence that it can hybridize to the given nucleotide sequence thereby forming a stable duplex under high stringency or stringent hybridization conditions.

In another embodiment, the invention provides an isolated nucleic acid molecule comprising at least 12 sequential nucleotides of SEQ ID NO: 3 or SEQ ID NO:5, or the complement thereof. Such an isolated nucleic acid molecule can be used as a nucleic acid probe for identifying and/or cloning homologues of COX-3 in other cell types, e.g., from other tissues, as well as homologues from other mammals. The probe/primer typically comprises a nucleotide sequence that hybridizes under stringent conditions to at least about 12, 25, 50, 75, or 90 consecutive nucleotides of the sense or anti-sense sequence of SEQ ID NO:3 or SEQ ID NO:5.

In a preferred embodiment, the invention provides an isolated nucleic acid molecule comprising the nucleotide sequence of SEQ ID NO:8 or SEQ ID NO:10, or a complement thereof.

In another preferred embodiment, the invention provides an isolated nucleic acid molecule comprising a nucleotide sequence encoding a polypeptide of SEQ ID No:9 or SEQ ID NO:11, or a complement thereof. For example, the invention provides an isolated nucleic acid molecule comprising a nucleic acid molecule which is a conserved substitution of human COX-3 cDNA as set forth in SEQ ID NO:8 or SEQ ID NO:10, or a complement thereof. It is known that more than one genetic codon can be used to encode a particular amino acid, and therefore, the amino acid sequence of human COX-3 as depicted in SEQ ID NO:9 or SEQ ID NO:11 can be encoded by any of a set of similar DNA molecules. Only one member of the set will be identical to the cDNA sequence as set forth in SEQ ID NO: 8 or SEQ ID NO:10. However all variants hereinafter referred to as degenerate variants are contemplated within the scope of this invention. Herein, a nucleic acid molecule bearing one or more alternative codons which encodes a polypeptide with the amino acid sequence set forth as SEQ ID NO:9 or SEQ ID NO:11, is defined as a conserved substitution of the human COX-3 DNA as set forth in SEQ ID NO:8 or SEQ ID NO:10, respectively.

Particularly preferred in this regard are natural allelic variants of human COX-3 nucleic acid molecules. DNA sequence polymorphisms that lead to changes in the amino acid sequence can exist within a population (e.g., the human population). Such genetic polymorphisms can exist among individuals within a population due to natural allelic variation. An allele is one of a group of genes that occur alternatively at a given genetic locus. Such natural allelic variations can typically result in 1-5% variance in the nucleotide sequence of a given gene. Alternative alleles can be identified by sequencing the gene of interest in a number of different individuals, or by using hybridization probes to identify the same genetic locus in a variety of individuals.

Further particularly preferred in this regard are nucleic acid molecules having any and all such nucleotide variations that are not known to occur naturally which encode polypeptides having properties that are different than, but still maintain the functional activity of, the naturally occurring human COX-3 protein. In addition to a naturally occurring variant such as a naturally occurring allelic variant, a variant of the polynucleotide or polypeptide can also be a variant that is not known to occur naturally. DNA sequences can be altered manually so as to code for a peptide having properties that are different from those of the naturally occurring peptide. Methods of altering the DNA sequences include, but are not limited to, site directed mutagenesis, chimeric substitution, and gene fusions. Site-directed mutagenesis is used to change one or more DNA residue that can result in a silent mutation, a conservative mutation, or a nonconservative mutation. Chimeric genes are prepared by swapping domains of similar or different genes to replace similar domains in the COX-3 gene. Similarly, fusion genes can be prepared that add domains to the COX-3, such as an affinity tag to facilitate identification and isolation of the gene and protein.

The variants of the human COX-3 nucleic acid molecule of the invention are capable of hybridizing to SEQ ID NO:3 or SEQ ID NO:5 under high stringent hybridization condition.

Yet another preferred embodiment of the nucleic acid molecule of the invention are siRNAs corresponding to the human COX-3 gene. Many organisms possess mechanisms to silence gene expression when double-stranded RNA (dsRNA) corresponding to the gene is present in the cell through a process known as RNA interference. The technique of using dsRNA to reduce the activity of a specific gene was first developed using the worm *C. elegans* and has been termed RNA interference, or RNAi (Fire, et al., (1998), *Nature* 391: 806-811). RNAi has since been found to be useful in many organisms, and recently has been extended to mammalian cells (see review by Moss, (2001), *Curr Biol* 11: R772-5).

An important advance was made when RNAi was shown to involve the generation of small RNAs of 21-25 nucleotides (Hammond et al., (2000) *Nature* 404: 293-6; Zamore et al., (2000) *Cell* 101: 25-33). These small interfering RNAs, or siRNAs, may initially be derived from a larger dsRNA that begins the process, and are complementary to the target RNA that is eventually degraded. The siRNAs are themselves double-stranded with short overhangs at each end. They act as guide RNAs, directing a single cleavage of the target in the region of complementarity (Elbashir et al., (2001) *Genes Dev* 15: 188-200; Zamore et al., (2000) *Cell* 101: 25-33).

Preferably, the siRNAs of the invention comprises about 21-25 nucleotides that are complementary to COX-1 intron 1 nucleotide sequence shown in SEQ ID NO:3 or SEQ ID NO:5.

Methods of producing siRNA, preferably 21-23 nucleotides (nt) in length from an in vitro system and use of the siRNA to interfere with mRNA of a gene in a cell or organism are described in WO0175164 A2.

The siRNA can also be made in vivo from a mammalian cell using a stable expression system. For example, a vector system, named pSUPER, that directs the synthesis of siRNAs in mammalian cells, was reported (Brummelkamp et al., (2002) Science 296: 550-3.).

The present invention provides methods of isolating human COX-3 nucleic acid molecules. Cells or tissues that possess human COX-3 transcript, preferably high levels of hCOX-3 transcript, are suitable for the isolation of hCOX-3 cDNA or mRNA. Selection of a suitable cDNA source can be performed by screening for the presence of hCOX-3 transcripts in cell extracts or in whole cells by nucleotide hybridization or RT-PCR analysis using primers that hybridize specifically to COX-1 intron 1 transcript as depicted in SEQ ID NO: 3 or SEQ ID NO:5. An exemplary source for COX-3 nucleic acid isolation is cerebral cortex.

Any of a variety of procedures known in the art can be used to isolate a nucleic acid molecule encoding a human COX-3 protein. For example, using cDNA or genomic DNA libraries, or total mRNA from the suitable cells identified above as a template and appropriate oligonucleotide as primers, a nucleic acid molecule of the invention can be amplified according to standard PCR amplification techniques. The nucleic acid so amplified from PCR can be cloned into an appropriate vector and characterized by DNA sequence analysis. The ordinarily skilled artisan will appreciate that oligonucleotides comprising at least 12 contiguous nucleotides of SEQ ID NO:3 or SEQ ID NO:5 are particularly useful as primers. The primers can be prepared by standard synthetic techniques, e.g., using an automated DNA synthesizer. Particularly preferred primers are those that can be used to detect an hCOX-3 gene but do not bind to other known COX genes, such as COX-1 or COX-2.

Another method to isolate hCOX-3 nucleic acid molecules is to probe a genomic or cDNA library, or alternatively total mRNA with one or more natural or artificially designed probes using procedures recognized by those familiar with the art. See, e.g., "Current Protocols in Molecular Biology", Ausubel et al. (eds.) Greene Publishing Association and John Wiley Interscience, New York, 1989, 1992. The ordinarily skilled artisan will appreciate that oligonucleotides comprising at least 12 contiguous nucleotides of SEQ ID NO:3 or SEQ ID NO:5 are particularly useful probes. Probes can have different length, such as at least 20, 30, 40 or 50 bases. It is also appreciated that such probes can be and are preferably labeled with an analytically detectable reagent to facilitate identification of the probe. Useful reagents include, but ate not limited to, radioisotopes, fluorescent dyes or enzymes capable of catalyzing the formation of a detectable product. The probes enable the ordinarily skilled artisan to isolate complementary copies of genomic DNA, cDNA or RNA polynucleotides encoding COX-3 proteins from human, mammalian or other animal sources or to screen such sources for related sequences, e.g., additional members of the family, type and/or subtype, including transcriptional regulatory and control elements as well as other stability, processing, translation and tissue specificity-determining regions from the regions that are 5' and/or 3' relative to the coding sequences disclosed herein, all without undue experimentation.

Another method to prepare nucleic acid molecules corresponding to all or a portion of a nucleic acid molecule of the invention is by standard synthetic techniques, e.g., using an automated DNA synthesizer.

Another method to isolate hCOX-3 nucleic acid molecules is by using a reverse genetics method. In this example, the COX-3 is purified and the partial amino acid sequence is determined by automated amino acid sequenators. It is not necessary to determine the entire length of a particular amino acid sequence, but the linear sequence of two regions of 4 to 8 amino acids from the protein is necessary for the production of primers for PCR amplification of a partial COX-3 cDNA fragment. Once suitable amino acid sequences have been identified, the DNA sequences capable of encoding them can either be synthesized by standard synthetic techniques, e.g., using an automated DNA synthesizer, or by degenerate PCR according to established PCR amplification techniques using cDNA or genomic DNA libraries, or total mRNA as a template and 15 to 30 degenerate oligonucleotides deduced from the amino acid sequence as primers. Because more than one genetic codon can be used to encode a particular amino acid, the amino acid sequence can be encoded by any of a set of similar DNA oligonucleotides. Thus, the frequency of codon usage in a particular host is taken in to account in designing the degenerate PCR primers based on known amino acid sequence. Often, each primer contains a pool of oligonucleotides to encourage specific hybridization to the template DNA. Although maximally only one member of the pool will be identical to the hCOX-3 sequence and will be capable of hybridizing to hCOX-3 DNA, slightly mismatched primers are also able to hybridize to the hCOX-3 DNA under moderately stringent hybridization conditions to initiate a PCR amplification reaction.

Preparation of cDNA libraries from the identified source cell can also be performed by standard techniques well known in the art. Well known cDNA library construction techniques can be found for example, in Maniatis et al., Molecular Cloning: A Laboratory Manual, Second Edition (Cold Spring Harbor Laboratory, Cold Spring Harbor, N.Y., 1989).

Isolation of total mRNA from the identified source cell can be performed by standard techniques well known in the art. Well known techniques of total mRNA isolation can be found for example, in Maniatis et al., supra.

Construction of genomic DNA libraries can be performed by standard techniques well known in the art. Well known genomic DNA library construction techniques can be found in Maniatis et al., supra.

Recombinant Expression Vectors and Host Cells

Another aspect of the invention pertains to vectors, preferably expression vectors, containing a nucleic acid the invention.

The recombinant expression vectors of the invention comprise a nucleic acid of the invention in a form suitable for expression of the nucleic acid in a host cell. The recombinant expression vectors include one or more regulatory sequences, selected on the basis of the host cells to be used for expression. These regulatory sequences are operably linked to the nucleic acid sequence to be expressed. Within a recombinant expression vector, the term "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). It will be appreciated by those skilled in the art that the design of the expression vector can depend on factors such as the choice of the host cell to be transformed, the level of expression of protein desired, and other considerations that are known to those in the art of gene expression. The expression vectors of the invention can be introduced into host cells to produce proteins or peptides, including fusion proteins or peptides that are encoded by nucleic acids as described herein.

The recombinant expression vectors of the invention can be designed for expression of a polypeptide of the invention in prokaryotic (e.g., *E. coli*) or eukaryotic cells (e.g., insect cells, for example using baculovirus expression vectors), yeast cells or mammalian cells). Suitable host cells are known to those skilled in the art. Alternatively, the recombinant expression vector can be transcribed and translated in vitro, for example using T7 promoter regulatory sequences and T7 polymerase.

Expression of proteins in prokaryotes is often carried out in *E. coli* with vectors containing constitutive or inducible promoters directing the expression of either fusion or non-fusion proteins. Fusion vectors add a number of amino acids to a protein encoded by the vector, usually adding amino acids to the amino terminus of the recombinant protein. Such fusion vectors typically serve four purposes: 1) to increase expression of recombinant protein; 2) to increase the solubility of the recombinant protein; 3) to aid in the purification of the recombinant protein by acting as a ligand in affinity purification; 4) to facilitate detection of the recombinant protein by serving as a marker. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include PGEX (Pharmacia Biotech Inc; Smith et al., (1988), *Gene* 67:31-40), pMAL (New England Biolabs, Beverly, Mass.), pRIT5 (Pharmacia, Piscataway, N.J.), or pQE (Qiagen), which fuse glutathione S-transferase (GST), maltose binding protein, protein A, or poly-His, respectively, to the target recombinant protein. Such vectors are contemplated within the scope of the invention.

Examples of suitable inducible non-fusion *E. coli* expression vectors include pTrc (Amann et al., (1988), *Gene* 69:301-315) and pETIId (Studier et al., Gene Expression Technology: Methods in Enzymology 185, Academic Press, San Diego, Calif. (1990) 60-89). One strategy to maximize recombinant protein expression in *E. coli* is to express the protein in a host bacteria with an impaired capacity to proteolytically cleave the recombinant protein. Another strategy is to alter the nucleic acid sequence of the nucleic acid to be inserted into an expression vector so that the individual codons for each amino acid are those preferentially utilized in *E. coli*. Such alteration of nucleic acid sequences of the invention can be carried out by standard DNA synthesis techniques.

In another embodiment, the expression vector is a yeast expression vector. Examples of vectors for expression in yeast *S. cerivisae* include for example, pYepSec1 (Baldari et al., (1987), *EMBO J* 6:229-234), pMFa (KurJan et al., (1982), *Cell* 30:933-943), pJRY88 (Schultz et al., (1987), *Gene* 54:113-123), pYES2 (Invitrogen Corporation, San Diego, Calif.), and pPicZ or *Pichia* (Invitrogen Corp, San Diego, Calif.).

Alternatively, the expression vector is a baculovirus expression vector. Baculovirus vectors available for expression of proteins in cultured insect cells include, but are not limited to, the pAc series (Smith et al., (1983), *Mol. Cell Biol.* 3:2156-2165) and the pVL series (Lucklow et al., (1989), *Virology* 170:31-39), and pBlueBacIII (Invitrogen).

In yet another embodiment, the expression vector is a mammalian expression vector. When used in mammalian cells, the expression vector's control functions are often provided by viral regulatory elements. For example, commonly used promoters are derived from polyoma, Adenovirus 2, cytomegalovirus and Simian Virus 40. Examples of mammalian expression vectors include, but are not limited to, pCDM8 (Seed (1987) Nature 329:840) and pMT2PC (Kaufman et al., (1987), *EMBO J* 6:187-195). Commercially available mammalian expression vectors which can be suitable for recombinant COX-3 expression, include, but are not limited to, pMAMneo (Clontech), pcDNA3 (Invitrogen), pMClneo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565).

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., (1987), *Genes Dev.* 1:268-277), lymphoid-specific promoters (Calame et al., (1988), *Adv. Immunol.* 43:235-275), including promoters of T cell receptors (Winoto et al, (1989), *EMBO J* 8:729-733) and immunoglobulins (BaneiJi et al., (1983), *Cell* 33:729-740; Queen et al., (1983), *Cell* 33:741-748). Other promoters include neuron-specific promoters (e.g., the neurofilament promoter; Byme et al., (1989), *Proc. Natl. Acad. Sci. USA* 86:5473-5477), pancreas-specific promoters (Edlund et al., (1985), *Science* 230:912-916), and mammary gland-specific promoters (e.g., milk whey promoter; U.S. Pat. No. 4,873,316 and European Application Publication No. 264,166). Developmentally-regulated promoters also include, for example, the marine hox promoters (Kessel et al., (1990), *Science* 249:374-379) and the beta-fetoprotein promoter (Campes et al., (1989), *Genes Dev.* 3:537-546).

The invention further provides a recombinant vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be selected which is capable of directing the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (Reviews—Trends in Genetics, Vol. 1(1) 1986).

The invention also provides a recombinant vector system that directs the synthesis of small interfering RNAs (siRNAs) in mammalian cells. An exemplary vector system that directs the synthesis of siRNAs in mammalian cells is the pSUPER (Brummelkamp et al., 2002, supra). On the pSUPER, the H1-RNA promoter was cloned in front of the gene specific targeting sequence (19-nt sequences from the target transcript separated by a short spacer from the reverse complement of the same sequence) and five thymidines (T5) as a termination signal. The resulting transcript is predicted to fold back on itself to form a 19-base pair stem-loop structure, resembling that of C. elegans Let-7. The size of the loop (the short spacer) is preferably 9 bp. A small RNA transcript lacking a polyadenosine tail, with a well-defined start of transcription and a termination signal consisting of five thymidines in a row (T5) was produced. Most importantly, the cleavage of the transcript at the termination site is after the second uridine yielding a transcript resembling the ends of synthetic siRNAs, that also contain two 3' overhanging T or U nucleotides. The siRNA expressed from pSUPER is able to knock down gene expression as efficiently as the synthetic siRNA.

Specifically designed vectors allow the shuttling of DNA between hosts such as bacteria-yeast or bacteria-animal cells or bacteria-fungal cells or bacteria-invertebrate cells. Numerous cloning vectors are known to those of skill in the art and the selection of an appropriate cloning vector is a matter of choice. For other suitable expression systems for both prokaryotic and eukaryotic cells see chapters 16 and 17 of Maniatis et al., supra.

Another aspect of the invention pertains to recombinant host cells into which a recombinant expression vector of the invention has been introduced.

Cell lines derived from mammalian species which can be suitable for transfection and which are commercially available, include, but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171), Drosophila or murine L-cells, and HEK-293 (ATCC CRL1573), and monkey kidney cells.

Vector DNA can be introduced into prokaryotic or eukaryotic cells via conventional transformation or transfection techniques. As used herein, the terms "transformation" or "transfection" refers to a process by which cells take up foreign DNA and may or may not integrate that foreign DNA into their chromosome. Transfection can be accomplished, for example, by various techniques including calcium phosphate or calcium chloride co-precipitation, DEAE-dextran-mediated transfection, lipofection, or electroporation, protoplast fusion. Suitable methods for transforming or transfecting host cells can be found in Maniatis et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to a drug) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

In another embodiment, the expression characteristics of an endogenous hCOX-3 nucleic acid within a cell, cell line or microorganism, can be modified by inserting a DNA regulatory element heterologous to the endogenous gene of interest into the genome of a cell, a stable cell line or a cloned microorganism such that the inserted regulatory element is operatively linked with the endogenous gene and controls, modulates or activates the endogenous gene.

A heterologous regulatory element can be inserted into a stable cell line or cloned microorganism, such that it is operatively linked with and activates expression of endogenous hCOX-3 genes, using techniques, such as targeted homologous recombination, which is well known to those of skill in the art, and described e.g., in Chappel, U.S. Pat. No. 5,272, 071; PCT publication No. WO 91/06667, published May 16, 1991.

The recombinant host cells of the invention can also be used to produce nonhuman transgenic animals. For example, in one embodiment, a host cell of the invention is a fertilized oocyte or an embryonic stem cell into which a sequence encoding a polypeptide of the invention has been introduced. Such host cells can then be used to create non-human transgenic animals in which exogenous sequences encoding a polypeptide of the invention have been introduced into their genome or homologous recombinant animals in which endogenous sequences encoding a polypeptide of the invention have been altered. Such animals are useful for studying the function and/or activity of the polypeptide and for identifying and/or evaluating modulators of polypeptide activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. Clones of the non-human transgenic animals can also be produced according to the methods described in Wilmut et al., (1997), Nature 385: 810-813 and PCT Publication NOS. WO 97/07668 and WO 97/07669.

Isolated Polypeptides of the Present Invention

One other aspect of the invention pertains to substantially purified hCOX-3 polypeptides. The invention provides a substantially purified polypeptide that is capable of converting arachidonic acid to the prostaglandin precursor prostaglandin H2, and comprises an amino acid sequence that has greater than about 60% amino acid sequence identity, preferably about 65, 70, 75, 80, 85, 90, or 95% amino acid sequence identity, to SEQ ID NO: 4 or SEQ ID NO:6. The sequence identity between two polypeptides can be determined using the method described supra.

In a preferred embodiment, the polypeptides of the present invention comprise an amino acid sequence that is substantially identical to SEQ ID NO: 9 or SEQ ID NO:11.

The isolated polypeptide of the invention includes chimeric or fusion proteins. As used herein, a "chimeric protein" or "fusion protein" comprises all or part (preferably biologically active) of a polypeptide of the invention operably linked to all or part of a heterologous polypeptide (i.e., a polypeptide other than the same polypeptide of the invention). Within the fusion protein, the term "operably linked" is intended to indicate that the polypeptide of the invention and the heterologous polypeptide are fused in-frame to each other. The heterologous polypeptide can be fused to the N-terminus or C-terminus of the polypeptide of the invention.

One example of a useful fusion protein is a HAHis fusion protein in which the polypeptide of the invention is fused at the C-terminus to a tag made of HA and poly His. Such fusion proteins facilitate the detection and purification of a recombinant polypeptide of the invention.

The invention pertains to methods of expressing or isolating a polypeptide of the invention. In one embodiment, the polypeptide can be isolated from cells or tissue sources that express the protein naturally by an appropriate purification scheme using standard protein purification techniques. In another embodiment, polypeptides of the invention are produced by recombinant DNA techniques. Alternatively, a polypeptide of the invention can be synthesized in an in vitro translation and/or transcription system. Further alternatively, a polypeptide of the invention can be synthesized chemically using standard peptide synthesis techniques.

Polypeptides of the invention can be recombinantly expressed by cloning DNA molecules of the invention into an expression vector described supra, introducing such a vector into prokaryotic or eukaryotic host cells described herein, and growing the host cell under conditions suitable for production of recombinant hCOX-3 protein. The expression vector-containing cells are clonally propagated and individually analyzed to determine whether they produce hCOX-3 protein. Identification of hCOX-3 expressing host cell clones can be done by several means, including, but not limited to, immunological reactivity with anti-hCOX-3 antibodies, and the presence of host cell-associated hCOX-3 activity. The selection of the appropriate growth conditions and recovery methods are within the skill of the art. Techniques for recombinantly expressing a polypeptide are fully described in Maniatis, T. et al., supra, and are well known in the art.

Polypeptides of the invention can also be produced using an in vitro translation and/or transcription system. Such methods are known to those skilled in the art. For example, synthetic hCOX-3 mRNA or mRNA isolated from hCOX-3 producing cells can be efficiently translated in various cell-free systems, including, but not limited to, wheat germ extracts and reticulocyte extracts. Alternatively, the coding sequence of hCOX-3 cDNA can be cloned under the control of a T7 promoter. Then, using this construct as the template, hCOX-3 protein can be produced in an in vitro transcription and translation system, for example using a TNT T7 coupled Reticulocyte Lysate System such as that commercially available from Promega (Madison, Wis.).

Polypeptides of the invention can also be produced by chemical synthesis, such as solid phase peptide synthesis on an automated peptide synthesizer, using known amino acid sequences or amino acid sequences derived from the DNA sequence of the genes of interest. Such methods are known to those skilled in the art.

Human COX-3 protein can be purified by methods known to those skilled in the art. For example, hCOX-3 from natural host cells, or recombinant hCOX-3 from recombinant host can be purified from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography, lectin chromatography, HPLC, and FPLC, and antibody/ligand affinity chromatography.

For example, hCOX-3 protein can be separated from other cellular proteins by use of an immunoaffinity column made with monoclonal or polyclonal antibodies specific for nascent or fragment of hCOX-3. The antibody affinity columns are made by adding the antibodies to a gel support such that the antibodies form covalent linkages with the gel bead support. Preferred covalent linkages are made through amine, aldehyde, or sulfhydryl residues contained on the antibody. Methods to generate aldehydes or free sulfydryl groups on antibodies are well known in the art, for example, amine groups are reactive with, in one example, N-hydroxysuccinimide esters. The affinity resin is then equilibrated in a suitable buffer, for example phosphate buffered saline (pH 7.3), and the cell culture supernatants or cell extracts containing hCOX-3 are slowly passed through the column. The column is then washed with the buffer until the optical density ($A_{280}$) falls to background. The protein is then eluted by changing the buffer condition, such as by lowering the pH using a buffer such as 0.23 M glycine-HCl (pH 2.6). The purified hCOX-3 protein is then dialyzed against a suitable buffer such as phosphate buffered saline.

Antibodies for Polypeptide of the Present Invention

Another aspect of the invention pertains to an antibody binding specifically to a human COX-3 of the invention. Particularly the antibody binds specifically to a polypeptide with an amino acid sequence that has greater than about 60% amino acid sequence identity, preferably about 65, 70, 75, 80, 85, 90, or 95% amino acid sequence identity, to SEQ ID NO:4 or SEQ ID NO:6. Preferably, the antibody of the present invention will not recognize a human COX-1 or human COX-2, but only human Cox-3. In various embodiments, the substantially purified antibodies of the invention, or fragments thereof, can be human, non-human, chimeric and/or humanized antibodies. Such antibodies and antibody fragments of the invention can be derived from a variety of sources, such as but not limited to, goat, mouse, rat, sheep, horse, chicken, or rabbit, antibodies. The antibodies relating to the invention can be polyclonal or monoclonal antibodies.

An isolated polypeptide comprising the amino acid sequence of SEQ ID NO:4 or SEQ ID NO:6, or a fragment thereof, which can be used as an immunogen to generate antibodies using standard techniques for polyclonal and monoclonal antibody preparation. Particularly preferred immunogen compositions are those that contain no other animal proteins such as, for example, immunogen recombinantly expressed from a non-animal host cell, i.e., a bacterial host cell, or a chemically synthesized oligopeptide.

Polyclonal antibodies can be raised by immunizing suitable subject animals such as mice, rats, guinea pigs, rabbits, goats, horses and the like, with rabbits being preferred, with the immunogen of the invention with or without an immune adjuvant. Pre-immune serum can be collected prior to the first immunization. Preferably, each animal receives between about 0.001 mg and about 1000 mg of the immunogen associated with or without an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of immunogen in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the antigen in Freund's incomplete adjuvant by the same route. Booster injections are given at about three-week intervals until maximal titers are obtained. At about 7 days after each booster immunization or about weekly after a single immunization, the animals are bled, the serum collected, and aliquots are stored at about −20° C.

Monoclonal antibodies (mAb) are prepared by immunizing inbred mice, preferably Balb/c, with the immunogen. The mice are immunized by the IP or SC route with about 0.001 mg to about 1.0 mg, preferably about 0.1 mg, of the immunogen in about 0.1 ml buffer or saline incorporated in an equal volume of an acceptable adjuvant, as discussed above. Freund's adjuvant is preferred, with Freund's complete adjuvant being used for the initial immunization and Freund's incomplete adjuvant used thereafter. The mice receive an initial immunization on day 0 and are allowed to rest for about 2 to about 30 weeks. Immunized mice are given one or more booster immunizations of about 0.001 to about 1.0 mg of human COX-3 or a fragment thereof in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions that will allow the formation of stable hybridomas. Fusion partners may include, but are not limited to: mouse myelomas P3/NS1/Ag 4-1; MPC-11; S-194 and Sp2/0, with Sp2/0 being generally preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using the human COX-3 or a fragment thereof as the antigen. The culture fluids can also be tested in the Ouchterlony precipitation assay to determine the isotype of the mAb. Hybridoma cells from antibody positive wells are cloned by a known technique such as the soft agar technique of MacPherson, Soft Agar Techniques, in Tissue Culture Methods and Applications, Kruse and Paterson, Eds., Academic Press, 1973 or by the technique of limited dilution.

Monoclonal antibodies are produced in vivo by injection of pristane primed Balb/c mice, approximately 0.5 ml per mouse, with about $1 \times 10^6$ to about $6 \times 10^6$ hybridoma cells at least about 4 days after priming. Ascites fluid is collected at approximately 8-12 days after cell transfer and the monoclonal antibodies are purified by techniques known in the art.

Monoclonal Ab can also be produced in vitro by growing the hydridoma in tissue culture media well known in the art. High density in vitro cell culture can be conducted to produce large quantities of mAbs using hollow fiber culture techniques, air lift reactors, roller bottle, or spinner flasks culture techniques well known in the art. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of COX-3 in body fluids or tissue and cell extracts.

The antibody molecules can be isolated from the mammal (e.g., from the blood) or culture cells and further purified by well-known techniques, such as protein A chromatography to obtain the IgG fraction. Alternatively, antibodies specific for a protein or polypeptide of the invention can be selected for (e.g., partially purified) or purified by, e.g., affinity chromatography. For example, a recombinantly expressed and purified (or partially purified) protein of the invention is produced as described herein, and covalently or non-covalently coupled to a solid support such as, for example, a chromatography column. The column can then be used to affinity purify antibodies specific for the proteins of the invention from a sample containing antibodies directed against a large number of different epitopes, thereby generating a substantially purified antibody composition, i.e., one that is substantially free of contaminating antibodies. By a substantially purified antibody composition is meant, in this context, that the antibody sample contains at most only 30% (by dry weight) of contaminating antibodies directed against epitopes other than those on the desired protein or polypeptide of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired protein or polypeptide of the invention.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions are derived from different animal species, such as those having a variable region derived from a murine mAb and a human immunoglobulin constant region (See, e.g., Cabilly et al., U.S. Pat. No. 4,816,567). Humanized antibodies are antibody molecules from non-human species having one or more complementarily determining regions (CDRs) from the non-human species and a framework region from a human immunoglobulin molecule (See, e.g., Queen, U.S. Pat. No. 5,585,089). Such chimeric and humanized monoclonal antibodies can be produced by recombinant DNA techniques known in the art, for example using methods described in PCT Publication No. WO 87/02671.

Completely human antibodies are particularly desirable for therapeutic treatment of human patients. Such antibodies can be produced, for example, using transgenic mice which are incapable of expressing endogenous immunoglobulin heavy and light chains genes, and which can also express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg et al., (1995), *Int. Rev. Immunol.* 13:65-93).

Completely human antibodies which recognize a selected epitope can be generated using a technique referred to as "guided selection". In this approach a selected non-human monoclonal antibody, e.g., a mouse antibody, is used to guide the selection of a completely human antibody recognizing the same epitope (Jespers et al., (1994), *Bioltechnology* 12:899-903).

The antibody of the invention (e.g., monoclonal antibody) can be used to isolate the polypeptide of the invention by standard techniques, such as affinity chromatography or immunoprecipitation. Moreover, such an antibody can be used to detect the protein (e.g., in a cellular lysate or cell supernatant, or cell membrane preparation) in order to evaluate the abundance and pattern of expression of the polypeptide. The antibodies can also be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^3H$.

Further, an antibody (or fragment thereof) can be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, I-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCN-LJ), cyclothosphamide, busulfan, dibromomannitol, streptozotocin, mitomycin C, and cis-dichlorodiamine platinum (11) (DDP) cisplatin), anthracyclines (e.g., daunorubicin (formerly daunomycin) and doxorabicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety can be a protein or polynucleotide possessing a desired biological activity. Alternatively, an antibody can be conjugated to a second antibody to form an antibody heteroconjugate as described by Segal in U.S. Pat. No. 4,676,980.

Methods of Detection

The present invention also relates to methods of detecting a polypeptide or nucleic acid of the invention in a sample. The sample can be any type of sample, including but not limited to, a biological sample taken from a subject, a chemically synthesized sample, and a substantially purified sample. Such assays can be used for diagnostic purposes.

In one embodiment, the invention provides a method of detecting a nucleic acid molecule of a human COX-3 gene, comprising the step of contacting a sample with a nucleic acid probe that hybridizes specifically to a nucleic acid molecule with the sequence of SEQ ID NO:3 or SEQ ID NO:5 under stringent conditions and detecting the probe-nucleic acid molecule complex. Methods for detecting a nucleic acid molecule are known to those skilled in the art, including, but not limited to, Northern or Southern hybridization, in situ hybridization, and RT-PCR.

In another embodiment, the invention provides a method of detecting a human COX-3 protein, comprising the step of contacting a sample with an antibody that selectively binds to a polypeptide having at least 70%, 80% or 90% sequence identity to SEQ ID NO:4 or SEQ ID NO:6, and detecting the protein-antibody complex. Methods for detecting a polypeptide are known to those skilled in the art, including, but not limited to, enzyme linked immunosorbent assays (ELISAs), Western blots, immunoprecipitations, and immunohistochemistry.

The hCOX-3 protein can also be detected by determining the cyclooxygenase-3 activity within a sample. Such an assay comprises the steps of: a) incubating a test sample with an agent that is more potent at inhibiting cyclooxygenase-3 than either cyclooxygenase-1 or -2; b) exposing a substrate for cyclooxygenase to the test sample; and c) determining the cyclooxygenase activity of the test sample and comparing it with that of a control wherein the test sample is exposed to the substrate for cyclooxygenase and is not exposed to the agent that is more potent at inhibiting cyclooxygenase-3 than either cyclooxygenase-1 or -2.

The agent that is more potent at inhibiting cyclooxygenase-3 than either cyclooxygenase-1 or COX-2 is known in the art based on studies of the dog COX-3 (Chandrasekharan et al., 2002, supra). Such an agent can be selected from acetaminophen, phenacetin, dipyrone, Aspirin, diclofenac, ibuprofen, or the like.

Because the agents listed above preferentially inhibit COX-3 activity, these agents will decrease the cyclooxygenase activity more in a sample comprising COX-3 than in a sample comprising COX-1 or COX-2.

Numerous methods can be used to determine the cyclooxygenase activity of a biological sample. In one preferred embodiment, the COX activity can be measured by the amount of prostanoids produced from the arachidonic acid using radiometric (Dyer et al., 1995, *Inflam. Res.* 44, S241) or immunoassay techniques (Reitz, et al., 1994, *J. Med. Chem.* 37: 3878-3881). Prostanoids produced from the arachidonic acid include, but are not limited to, $PGD_2$, $PGE_2$, $PGF_{2\alpha}$, $PGI_2$, and thromboxane $A_2$ ($TxA_2$). In one example, the COX activity can be measured by the amount of $PGE_2$ produced from arachidonic acid by an enzyme immunoassay using a kit from Amersham Corp., BioTrak™ $PGE_2$. In another example, the COX activity can be measured by the amount of $PGF_{2\alpha}$ produced by SnCl reduction of COX-derived PGH2 via EIA, using a commercially available kit from Cayman Chemical Company (Cat No: 560131, or 560101). Alternatively, the COX activity can be measured by the amount of other prostanoids produced from the arachidonic acid using methods similar to those for measuring the amount of $PGE_2$ or $PGF_{2\alpha}$.

In another embodiment, the COX activity can be measured by determining the COX dependent oxygen consumption in the presence of substrate (Schewe et al., 1991, Pharmazie, 46, 804-809; Hsuanyu et al., 1992, *J. Biol. Chem.* 267, 17649-17657).

In another preferred embodiment, the COX activity can be measured by peroxidase activity associated with the COX enzyme. The peroxidase activity catalyzes the subsequent reduction of hydroperoxide $PG_2$ to $PGH_2$. The peroxidase activity of COX can be measured using a reducing agent cosubstrate that is chromagenic, or fluorogenic, such as homovanillic acid (Percival et al., 1994, *Arch. Biochem. Biophys.* 315:111-118) or N,N,N',N'-tetramethylphenylenediamine (TMPD) (Copeland et al., 1994, *Proc. Natl. Acad. Sci. USA*, 91:11202-11206). Alternatively, the peroxidase activity of COX can be measured by luminol (5-amino-2, 3-dihydro-1-4-phthalazinedione) reduction in real-time luminescence assays (Farnaz et al., 1998, *Anal. Biochem.* 264:216-221).

Various commercially available kits can be used to measure the peroxidase activity associated with COX. For example, a peroxidase-induced luminol luminescence assay kit is available from Assay Designs, Inc., (Cat No: 907-003); and a chemiluminescent assay kit is available from Cayman Chemical Company (Cat No: 760101); and a colorimetric assay kit from Cayman Chemical Company (Cat No: 760111).

The invention also encompasses kits for detecting the presence of a polypeptide or nucleic acid of the invention in a biological sample (a test sample). Such kits can be used to determine if a subject is suffering from or is at increased risk of developing a disorder related to hCOX-3. Such a kit preferably comprises a compartmentalized carrier suitable to hold in close confinement at least one container. The carrier can contain a means for detection such as labeled antigen or enzyme substrates or the like. For example, the kit can comprise a labeled compound or agent capable of detecting the polypeptide or mRNA encoding the polypeptide and means for determining the amount of the polypeptide or mRNA in a sample (e.g., an antibody which binds the polypeptide or an oligonucleotide probe which binds to DNA or mRNA encoding the polypeptide). The kits can also include instructions for determining whether a test subject is suffering from or is at risk of developing a disorder associated with aberrant expression of the polypeptide if the amount of the polypeptide or mRNA encoding the polypeptide is above or below a normal level.

For antibody-based kits, the kit can comprise, for example: (1) a first antibody (for example, an antibody attached to a solid support), which binds selectively to a polypeptide comprising an amino acid sequence having at least 70% sequence identity to SEQ ID NO:4 or SEQ ID NO:6; and, optionally; (2) a second antibody which binds to either the first antibody or the polypeptide that the first antibody binds to at a different epitope, and the second antibody is conjugated to a detectable agent; and (3) a purified recombinant hCOX-3 protein as positive control. Preferably, the first antibody only binds to a human COX-3, but not a human COX-1 or human COX-2, or COX-3 from other species, such as dog.

For hCOX-3 activity-based kits, the kit can comprise, for example: (1) an agent that is more potent at inhibiting COX-3 than either COX-1 or -2; (2) a substrate for COX-3; (3) means that can be used to detect the COX activity, and (4) a purified recombinant hCOX-3 protein as a positive control. The agent that is more potent at inhibiting cyclooxygenase-3 than either cyclooxygenase-1 or COX-2 can be selected from acetaminophen, phenacetin, dipyrone, Aspirin, diclofenac, ibuprofen, or the like. The substrate for COX-3 can be arachidonic acid coupled, or arachidonic acid coupled with a reducing agent cosubatrate that is chromagenic, fluorogenic, or capable of generating luminescent when catalyzed by the peroxidase activity of COx-3. Such reducing agent cosubstrates include, but are not limited to, homovanillic acid, TMPD, luminol, and the like. The means that can be used to detect the COX activity can be the means to detect the produced prostanoids from arachidonic acid by EIA or to detect the chromagenic, fluoregenic, or luminescent reaction resulting from the reducing agent cosubstrate.

For oligonucleotide-based kits, the kit can comprise, for example: (1) an oligonucleotide, e.g., a detectably labeled oligonucleotide, which hybridizes to a nucleic acid sequence having at least 80% sequence identity to SEQ ID NO: 3 or SEQ ID NO:5, or (2) a pair of primers useful for amplifying a nucleic acid molecule encoding a polypeptide having at least 70% sequence identity to SEQ ID NO:4 or SEQ ID NO:6. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample. Each component of the kit is usually enclosed within an individual container and all of the various containers are preferably contained within a single package.

The invention also provides a method to detect genetic lesions or mutations in an hCOX-3 gene. In preferred embodiments, the methods comprises the steps of: (a) isolating a human cyclooxygenase-3 polynucleotide from the sample; and (b) sequencing the human cyclooxygenase-3 polynucleotide to detect alterations in the gene sequence.

Examples of genetic mutations or genetic lesions of interest include, but are not limited to detection of: 1) a deletion of one or more nucleotides from the gene; 2) an addition of one or more nucleotides to the gene; 3) a substitution of one or more nucleotides of the gene; 4) a chromosomal rearrangement of the gene; 5) an alteration in the level of a messenger RNA transcript of the gene; 6) an aberrant modification of the gene, such as of the methylation pattern of the genomic DNA; 7) the presence of a non-wild type splicing pattern of a messenger RNA transcript of the gene; 8) a non-wild type level of a the protein encoded by the gene; 9) an allelic loss of the gene; and 10) an inappropriate post-translational modification of the protein encoded by the gene. Methods for detecting these genetic lesions or mutations are well known in the art. There are a large number of assay techniques known in the art which can be used for detecting lesions in a gene, such as PCR reactions, restriction enzyme cleavage patterns, hybridizing a sample and control nucleic acids, sequencing reactions, alterations in electrophoretic mobility, selective oligonucleotide hybridization, selective amplification, and selective primer extension.

Method of Treatment Using Gene Therapy

The present invention provides methods of treating a subject at risk of or suffering from a disorder related to hCOX-3 by increasing or decreasing the expression of hCOX-3 using gene therapy.

In dogs, the COX-3 is selectively inhibited by analgesic/antipyretic drugs, such as acetaminophen, suggesting that COX-3 may be the target of this type of drugs (Chandrasekharan et al., 2002, supra). Therefore, it is foreseeable that decreasing the expression of COX-3 via gene therapy will achieve similar therapeutic effects as those obtained with acetaminophen-type drugs, such as reducing the fever and relieving the pain. Gene therapy is preferred in treating chronic pain or fever when continuous administration of analgesics is required. Particularly because as with all NSAIDs, the analgesic action of acetaminophen is limited by a ceiling effect, when an increase in dose produces only a minor increment in effect (Beaver, 1988, *Am J. Med.*, 84 (Suppl 5A): 3-15).

In addition, statistically significant inverse association was found between the use of acetaminophen and ovarian cancer risk (Cramer et al., 1998, Lancet 351:104-7). Therefore decreasing the expression of human COX-3 via gene therapy may be a useful therapy in lowing death rate from ovarian cancer based on results from a prospective study that women who reported taking acetaminophen daily had a 45% lower death rate from ovarian cancer than women reporting no use (Rodriguez et al., 1998, Lancet 352:1354-5).

In one embodiment, COX-3 antisense therapy can be used to decrease the expression of hCOX-3 in a cell. COX-3 antisense therapy is particularly useful when decreased hCOX-3 activity is desirable.

The principle of antisense-based strategies is based on the hypothesis that sequence-specific suppression of gene expression can be achieved by intracellular hybridization between mRNA and a complementary antisense species. The formation of a hybrid RNA duplex can then interfere with the processing/transport/translation and/or stability of the target COX-3 mRNA. Hybridization is required for the antisense effect to occur. Antisense strategies can use a variety of approaches including the use of antisense oligonucleotides, injection of antisense RNA and transfection of antisense RNA expression vectors. Phenotypic effects induced by antisense hybridization to a sense strand are based on changes in criteria such as protein levels, protein activity measurement, and target mRNA levels.

An antisense nucleic acid can be complementary to an entire coding strand of an hCOX-3 gene, or to only a portion thereof. An antisense nucleic acid molecule can also be complementary to all or part of a non-coding region of the coding strand of a hCOX-3 gene. The non-coding regions ("5' and 3' UTRs") are the 5' and 3' sequences which flank the coding region and are not translated into amino acids. Preferably, the non-coding region is a regulatory region for the transcription or translation of the hCOX-3 gene.

An antisense oligonucleotide can be, for example, about 15, 25, 35, 45 or 65 nucleotides or more in length taken from the complementary sequence of SEQ ID NO: 3 or SEQ ID NO:5. It is preferred that the sequence be at least 18 nucleotides in length in order to achieve sufficiently strong annealing to the target mRNA sequence to prevent translation of the sequence. (Izant et al., 1984, *Cell*, 36:1007-1015; Rosenberg et al., 1985, *Nature*, 313:703-706). An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxytnethylaminomethyl-2-thiouridine, 5-carboxymethylaminomethyluracil, dihydrouracil, beta-D-galactosylqueosine, inosine, N6-isopentenyladenine, I-methylguanine, 1-methylinosine, 2,2-dimethylguanine, 2-methyladenine, 2-methylguanine, 3-methylecytosine, .5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. An antisense nucleic acid molecule can be a CC-anomeric nucleic acid molecule. A CC-anomeric nucleic acid molecule forms specific double-stranded hybrids with complementary RNA in which, contrary to the usual P-units, the strands run parallel to each other (Gaultier et al. (1987) *Nucleic Acids Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

Alternatively, the antisense nucleic acid can also be produced biologically using an expression vector into which a nucleic acid has been subcloned in an antisense orientation as described supra. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. To achieve sufficient intracellular concentrations of the antisense molecules, vector constructs in which the antisense nucleic acid molecule is placed under the control of a strong pol II or pol III promoter are preferred. For a discussion of the regulation of gene expression using antisense genes see Weintraub et al. (1985, *Trends in Genetics*, Vol. 1(1), pp. 22-25).

Typically, antisense nucleic acid is administered to a subject by microinjection, liposome encapsulation or generated in situ by expression from vectors harboring the antisense sequence. An example of a route of administration of antisense nucleic acid molecules includes direct injection at a tissue site. The antisense nucleic acid can be ligated into viral vectors that mediate transfer of the antisense nucleic acid when the viral vectors are introduced into host cells. Suitable viral vectors include retrovirus, adenovirus, adeno-associated virus, herpes virus, vaccinia virus, polio virus and the like. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens.

Once inside the cell, antisense nucleic acid molecules hybridize with or bind to cellular mRNA and/or genomic DNA encoding a COX-3 protein to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix.

In a preferred embodiment, when it is beneficial to decrease COX-3 activity, the method of decreasing the expression of COX-3 in a subject in need thereof involves the use of small interfering RNA (siRNA).

In several organisms, introduction of double-stranded RNA has proven to be a powerful tool to suppress gene expression through a process known as RNA interference. The siRNA corresponding to hCOX-3 and the methods of producing siRNA are described supra. The present invention provides a method of decreasing the expression of hCOX-3 in a cell of a subject in need thereof, comprising the steps of (a) introducing siRNA that targets the mRNA of the human COX-3 gene for degradation into the cell of the subject; (b) maintaining the cell produced in (a) under conditions under which siRNA interference of the mRNA of the human COX-3 gene in the cell of the subject occurs. The siRNA can be introduced into the cell of the subject using procedures similarly to those for the anti-sense nucleic acids described herein.

In another embodiment, gene therapy can be used to increase the expression of hCOX-3 by introducing a nucleic acid molecule capable of expressing a human COX-3 protein into the cells of a subject. COX-3 gene therapy can be particularly useful for the treatment of diseases where it is beneficial to elevate COX-3 activity.

A procedure for performing ex vivo gene therapy is outlined in U.S. Pat. No. 5,399,346 and also in exhibits submitted in the file history of that patent, all of which are publicly available documents. In general, gene therapy can involve introduction in vitro of a functional copy of a gene into a cell(s) of a subject, and returning the genetically engineered cell(s) to the subject. The functional copy of the gene is under operable control of regulatory elements, which permit expression of the gene in the genetically engineered cell(s). Numerous transfection and transduction techniques as well as appropriate expression vectors are well known to those of ordinary skill in the art, some of which are described in PCT application WO95/00654. In vivo gene therapy uses vectors such as adenovirus, retroviruses, vaccinia virus, bovine papilloma virus, and herpes virus such as Epstein-Barr virus. Gene transfer can also be achieved using non-viral means requiring infection in vitro. Such means can include calcium phosphate, DEAE dextran, electroporation, and protoplast fusion. Targeted liposomes can also be potentially beneficial for delivery of DNA into a cell.

As one example, a DNA molecule encoding a human COX-3 protein can be first cloned into a retroviral vector. The expression of COX-3 protein from the vector can be driven from its endogenous promoter or from the retroviral long terminal repeat or from a promoter specific for certain target cells. The vector can then be introduced into a cell of a subject to successfully express hCOX-3 proteins in the target cells. The gene can be preferably delivered to those cells in a form which can be used by the cell to encode sufficient protein to provide effective function. Retroviral vectors are often a preferred gene delivery vector for gene therapy especially because of their high efficiency of infection and stable integration and expression. Alternatively, hCOX-3 DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo as well as in vivo COX-3 gene therapy. Protocols for molecular methodology of gene therapy suitable for use with the hCOX-3 gene are described in Gene Therapy Protocols, edited by Paul D. Robbins, Human press, Totowa N.J., 1996.

During treatment, the effective amount of nucleic acid molecules of the invention administered to individuals can vary according to a variety of factors including type, species, age, weight, sex and medical condition of the patient; the severity of the condition to be treated; the route of administration; the renal and hepatic function of the patient; and the particular nucleic acid molecule thereof employed. A physician or veterinarian of specialized skill in gene therapy can determine and prescribe the effective amount required to prevent, counter or arrest the progress of the condition. Optimal precision in achieving concentrations within the range that yields efficacy without toxicity requires a regimen based on the kinetics of the nucleic acid molecule's availability to target sites. This involves a consideration of the distribution, equilibrium, and elimination of the nucleic acid molecule involved in gene therapy.

The gene therapy disclosed herein can be used alone at appropriate dosages defined by routine testing in order to obtain optimal increase or decrease of the hCOX-3 activity while minimizing any potential toxicity. In addition, co-administration or sequential administration of other agents may be desirable. The dosages of administration are adjusted when several agents are combined to achieve desired effects. Dosages of these various agents can be independently optimized and combined to achieve a synergistic result wherein the pathology is reduced more than it would be if either agent were used alone.

The present invention also contemplates a method of evaluating the mechanism of action of an analgesic/antipyretic drug in a cell, comprising the steps of:
  (a) administering to the cell an effective amount of a composition that increases or decreases the expression or activity of a human cyclooxygenase-3 in the cell;
  (b) administering to the cell a therapeutically effective amount of the analgesic/antipyretic drug;
  (c) measuring a therapeutic effect of the analgesic/antipyretic drug on the cell, and
  (d) comparing the therapeutic effect with that of a control.

In one embodiment the comparing step comprises comparing the therapeutic effect with that of a control wherein the expression or activity of human cyclooxygenase-3 in the cell has not been increases or decreases prior to the administration of the analgesic/antipyretic drug.

An analgesic/antipyretic drug that targets the human COX-3 inside a cell will show a clear distinction of its therapeutic effect when the level of COX-3 expression or activity is changed inside the cell. The level of COX-3 expression can be decreased by antisense or siRNA technique as described supra. The level of COX-3 expression can be increased by introducing a nucleic acid molecule capable of encoding a functional cyclooxygenase-3 protein into a cell in the subject. The level of hCOX-3 activity can be increased or decreased using an activator or inhibitor of hCOX-3, and the activator or inhibitor of hCOX-3 can be obtained using a compound identification method described infra.

Methods of Identifying Modulators of hCOX-3

"Inhibitors", "activators", and "modulators" of hCOX-3 refer to inhibitory or activating molecules identified using in vitro and in vivo binding assays for human COX-3. Preferably by measuring the cyclooxygenase activity of human COX-3.

In particular, "inhibitors" refer to compounds that decrease, prevent, inactivate, desensitize or down regulate COX-3 expression or activity. "Activators" are compounds that increase, activate, facilitate, sensitize or up regulate COX-3 expression or activity. "Modulators" include both the "inhibitors" and "activators".

The compound identification methods can be performed using conventional laboratory formats or in assays adapted for high throughput. The term "high throughput" refers to an assay design that allows easy screening of multiple samples simultaneously, and can include the capacity for robotic manipulation. Another desired feature of high throughput assays is an assay design that is optimized to reduce reagent usage, or minimize the number of manipulations in order to achieve the analysis desired. Examples of assay formats include 96-well or 384-well plates, levitating droplets, and "lab on a chip" microchannel chips used for liquid handling experiments. It is well known by those in the art that as miniaturization of plastic molds and liquid handling devices are advanced, or as improved assay devices are designed, that greater numbers of samples can be performed using the design of the present invention.

Candidate compounds encompass numerous chemical classes, although typically they are organic compounds. Preferably, they are small organic compounds. Candidate compounds comprise functional chemical groups necessary for structural interactions with polypeptides, and typically include at least an amine, carbonyl, hydroxyl or carboxyl group, preferably at least two of the functional chemical groups and more preferably at least three of the functional chemical groups. The candidate compounds can comprise cyclic carbon or heterocyclic structure and/or aromatic or polyaromatic structures substituted with one or more of the above-identified functional groups. Candidate compounds also can be biomolecules such as peptides, saccharides, fatty acids, sterols, isoprenoids, purines, pyrimidines, derivatives or structural analogs of the above, or combinations thereof and the like. Where the compound is a nucleic acid, the compound typically is a DNA or RNA molecule, although modified nucleic acids having non-natural bonds or subunits are also contemplated.

Candidate compounds are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Candidate compounds can also be obtained using any of the numerous approaches in combinatorial library methods known in the art, including: biological libraries; spatially addressable parallel solid phase or solution phase libraries: synthetic library methods requiring deconvolution; the "one-bead one-compound" library method; and synthetic library methods using affinity chromatography selection (Lam (1997) *Anticancer Drug Des.* 12:145). Alternatively, libraries of natural compounds in the form of bacterial, fungal, plant and animal extracts are available or readily produced. Additionally, natural and synthetically produced libraries and compounds can be readily modified through conventional chemical, physical, and biochemical means.

Further, known pharmacological agents can be subjected to directed or random chemical modifications such as acylation, alkylation, esterification, amidation, etc. to produce structural analogs of the agents. Candidate compounds can be selected randomly or can be based on existing compounds that bind to and/or modulate the function of COX-1 or COX-2 activity. Therefore, a source of candidate agents is libraries of molecules based on known COX activators or inhibitors in which the structure of the compound is changed at one or more positions of the molecule to contain more or fewer chemical moieties or different chemical moieties. The structural changes made to the molecules in creating the libraries of analog activators/inhibitors can be directed, random, or a combination of both directed and random substitutions and/or additions. One of ordinary skill in the art in the preparation of combinatorial libraries can readily prepare such libraries based on the existing NSAIDs, or analgesic/antipyretic compounds.

A variety of other reagents also can be included in the mixture. These include reagents such as salts, buffers, neutral proteins (e.g., albumin), detergents, etc. that can be used to facilitate optimal protein-protein and/or protein-nucleic acid binding. Such a reagent can also reduce non-specific or background interactions of the reaction components. Other reagents that improve the efficiency of the assay such as nuclease inhibitors, antimicrobial agents, and the like can also be used.

Examples of methods for the synthesis of molecular libraries can be found in the art, for example in: Zuckermann et al. (1994). *J Med. Chem.* 37:2678. Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (U.S. Pat. No. 5,223,409), spores (U.S. Pat. No. 5,571,698), plasmids (Cull et al. (1992) *Proc. Natl. Acad. Sci. USA* 89:1865-18.69) or phage (see e.g., Scott and Smith (1990) *Science* 249:3 86-390).

In one embodiment, the present invention provides a method of identifying a compound that increase or decrease prostaglandin synthesis catalyzed by a human COX-3, comprising the steps of: (a) contacting a human cyclooxygenase-3 protein, or a polypeptide comprising an active fragment of the human cyclooxygenase-3 protein, with a test compound and with a substrate for cyclooxygenase; and (b) determining the cyclooxygenase activity in (a), and comparing it with that of a control wherein the human cyclooxygenase-3 protein, or the polypeptide comprising an active fragment of the human cyclooxygenase-3 protein is only exposed to the substrate for cyclooxygenase but not the test compound. Compounds that are activators for hCOX-3 will increase the rate of substrate conversion and result in more COX activity in the sample compared to the control as a function of time. Compounds that are inhibitors of COX-3 will decrease the rate of substrate conversion and result in less COX activity in the sample compared to the control as a function of time.

In a preferred embodiment, the method of identifying a compound that increase or decrease prostaglandin synthesis catalyzed by a human COX-3 described supra, further comprises the step of testing whether the test compound changes the cyclooxygenase activity of another cyclooxygenase enzyme, such as human COX-1, or human COX-2. Preferably, the test compound only increases or decreases the cyclooxygenase activity of hCOX3, but not that of hCOX-1 or hCOX-2.

Numerous methods can be used to determine the cyclooxygenase activity of a biological sample, and they were described supra.

In one preferred embodiment, the COX protein used in the assay methods is associated with a host cell, native or recombinant. U.S. Pat. No. 5,837,479 claims a method for identifying a compound that inhibits COX-2 activity using a recombinant cell line for COX-2. Similar method can be used for identifying a compound that inhibits hCOX-3 activity using a host cell for hCOX-3. The term "cell" refers to at least one cell, but includes a plurality of cells appropriate for the sensitivity of the detection method. Preferably, cells suitable for the method of present invention are eukaryotic.

In another preferred embodiment, the COX protein used in the assays is part of an isolated membrane preparation. Like COX-1 or -2, COX-3 is a membrane protein. Membranes containing human COX-3 can be isolated from hCOX-3 host cells using methods known to those skilled in the art, and be used as the source of hCOX-3 in the screening assay.

In yet another preferred embodiment, the COX protein used in the assays can be purified or isolated.

In another preferred embodiment, binding assays can be used to identify a compound that binds to a human COX-3 protein, and potentially is capable of increasing or decreasing the biological activity of hCOX-3 protein. One exemplary method comprises the steps of: (a) incubating a test compound with a hCOX-3 protein and a labeled ligand for the hCOX-3 protein; (b) separating the hCOX-3 protein from unbound labeled ligand; and (c) identifying a compound that inhibits ligand binding to the subunit by a reduction in the amount of labeled ligand binding to the hCOX-3. An example of the labeled ligand for hCOX-3 protein is a labeled hCOX-3 specific antibody as described supra or an agent that is more potent at inhibiting hCOX-3 than either hCOX-1 or hCOX-2, such as acetaminophen, phenacetin, dipyrone, Aspirin, diclofenac, and ibuprofen. Preferably, a hCOX-3 host cell (recombinant or native) that expresses the hCOX-3 but not hCOX-1 or hCOX-2 can be used for the binding assay. More preferably, cell membranes prepared from the hCOX-3 host cell can be used for the binding assay. Further preferably, a substantially purified hCOX-3 protein can be used for the binding assay.

Separation of the hCOX-3 protein from unbound labeled ligand can be accomplished in a variety of ways. Conveniently, at least one of the components is immobilized on a solid substrate, from which the unbound components can be easily separated. The solid substrate can be made of a wide variety of materials and in a wide variety of shapes, e.g., microtiter plate, microbead, dipstick, resin particle, etc. The substrate preferably is chosen to maximize signal to noise ratios, primarily to minimize background binding, as well as for ease of separation and cost.

Separation can be effected for example, by removing a bead or dipstick from a reservoir, emptying or diluting a reservoir such as a microtiter plate well, or rinsing a bead, particle, chromatographic column or filter with a wash solution or solvent. The separation step preferably includes multiple rinses or washes. For example, when the solid substrate is a microtiter plate, the wells can be washed several times with a washing solution, that typically includes those components of the incubation mixture that do not participate in specific bindings such as salts, buffer, detergent, non-specific protein, etc. Where the solid substrate is a magnetic bead, the beads can be washed one or more times with a washing solution and isolated using a magnet.

A wide variety of labels can be used to label the ligand for hCOX-3, such as those that provide direct detection (e.g., radioactivity, luminescence, optical or electron density, etc.)., or indirect detection (e.g., epitope tag such as the FLAG epitope, enzyme tag such as horseradish peroxidase, etc.).

In more than one embodiment of the above assay methods of the present invention, it can be desirable to immobilize either the hCOX-3 or its ligand to facilitate separation of complexed from uncomplexed forms of the hCOX-3 protein, as well as to accommodate automation of the assay. Binding of a test compound to a polypeptide, or interaction of a polypeptide with a target molecule in the presence and absence of a candidate compound, can be accomplished in any vessel suitable for containing the reactants. Examples of such vessels include microtitre plates, test tubes, and microcentrifuge tubes. In one embodiment, a fusion protein of hCOX-3 can be provided which adds a domain that allows one or both of the hCOX-3 and its ligand to be bound to a matrix. For example, a fusion protein of hCOX-3 with glutathione-S-transferase can be adsorbed onto glutathione sepharose beads (Sigma Chemical; St. Louis, Mo.) or glutathione derivatized microtitre plates, which are then combined with the test compound or the test compound and the labeled ligand for hCOX-3, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of binding or activity of the polypeptide of the invention can be determined using standard techniques.

Other techniques for immobilizing proteins on matrices can also be used in the screening assays of the invention.

For example, either the hCOX-3 or its ligand can be immobilized utilizing conjugation of biotin and streptavidin.

Biotinylated polypeptide or target molecules can be prepared from biotin-NHS (N-hydroxy-suceinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with the hCOX-3 but which do not interfere with binding of the hCOX-3 to its target molecule can be derivatized to the wells of the plate and hCOX-3 can be trapped in the wells by antibody conjugation. Methods for detecting such complexes, in addition to those described above for the GST-immobilized complexes, include immunodetection of complexes using antibodies reactive with the polypeptide of the invention or target molecule, as well as enzyme-linked assays which rely on detecting an enzymatic activity associated with the polypeptide of the invention or target molecule.

It is understood that the present invention is not limited to the particular methodology, databases, gene sequences, and gene sequence analysis method, etc., described herein, as these may vary. It is also to be understood that the terminology used herein is not intended to limit the scope of the present invention. It must be noted that as used herein and in the appended claims, the singular forms "a," "an," and "the" include plural reference unless the context clearly dictates otherwise.

Thus, for example, a reference to "a gene" is a reference to one or more genes and includes equivalents thereof known to those skilled in the art and so forth. Indeed, one skilled in the art can use the methods described herein to identify and utilize any COX-3 gene and protein, known presently or subsequently. All references identified herein are incorporated into this document in their entirety.

EXAMPLE 1

Confirmation of the Intron 1 Sequence for Human Cox-1

Figure 1:
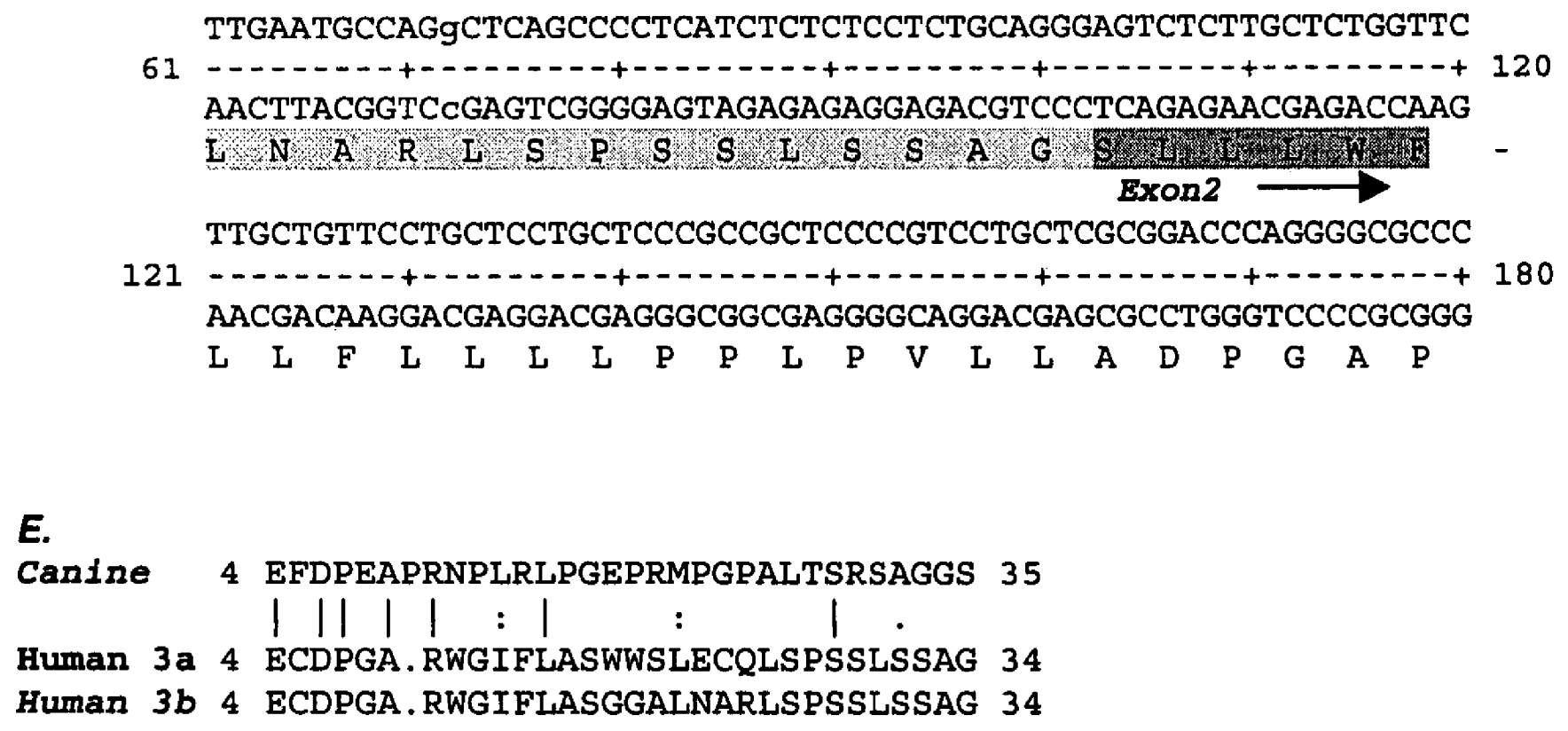

The full-length human COX-1 cDNA sequence (GenBank accession number: NM_000962) was used as a query to search the NCBI human genome database. The human COX-1 gene is localized on chromosome 9 and comprises 11 exons and 10 introns that span about 22 kb. The sequences of exon 1, intron 1 and exon 2 from NCBI are shown in FIG. 1A. If, like the canine Cox-3, the human Cox-3 retains the entire intron 1 of human COX-1, the sequence obtained from the human genomic database will be translationally out of frame. None of the three possible reading frames (a, b, and c) would result in a polypeptide that comprises the amino acid sequences encoded by exon 1, intron 1, and exon 2 of human Cox-1 (FIG. 1B). Therefore, the first question is whether the published human genomic sequence is indeed correct. Or whether the published genomic sequence contains a frame shift mutation that results in early termination of the translation.

Two oligonucleotides were designed for amplifying the genomic sequence of exon 1-intron 1-exon 2 of human COX-1. The forward primer was designed based on exon 1 and part of the intron 1 sequence, SEQ ID NO: 1, 5' ATGAGCCGT-GAGTGCGACCCCGGT 3', and the reverse primer was based on exon 2, SEQ ID NO: 2, 5' CTACCTG-GCGTGGGCGCCCCTGGGT 3'. The PCR was performed with the Advantage®-GC Genomic PCR kit purchased from BD Bioscience Clontech (Palo Alto, Calif.). The reaction mixture contained 1 μg of human genomic DNA (BD Bioscience Clontech, Palo Alto, Calif.), 10 μl of 5×GC Genomic reaction buffer, 0.5 M GC-Melt, 1.1 mM Mg(OAc)$_2$, 200 μM dNTP, 200 nM of each primer and 1 μl of 50× Advantage-GC genomic DNA polymerase mixture. The thermal cycler parameter for genomic PCR were: initial denaturing at 94° C.

for 1 min, 35 cycles of 94° C./30 sec. and 68° C./2 min. The PCR product (~190 bp fragment) was subcloned into pPCR-Script cloning vector (Stratagene, CA) and sequenced.

Sequence analysis indicated that the sequence of exon 1-intron 1-exon 2 of human COX-1 was consistent with that published in the human genome database. Therefore, if the entire intron 1 (94 bp) is retained in hCOX-3, there would be a shift in the reading frame, resulting in no production of an active COX3 enzyme in human tissues. At least two mechanisms could maintain an open reading frame, leading to the production of an active COX3 enzyme: 1) RNA editing, i.e., retention of the entire intron 1 followed by the removal of some nucleotides at the mRNA level; or 2) partial retention of intron 1.

EXAMPLE 2

Cloning of cDNA Encoding the N-Terminus of Human COX-3

To identify human COX-3, a cDNA fragment was amplified from human brain, stomach and leukemia chronic myelogenous cDNA libraries with the forward primer being the same as that used for amplifying the genomic DNA sequence, SEQ ID NO: 1, and the reverse primer that is located at approximately bp position 600 of human COX-1 SEQ ID NO: 7, 5'-TATGAACTTCCTCCTGAGCAGGAA-3'. The PCR was performed in a final volume of 50 µl, containing 5 µl of Marathon-Ready™ human brain cDNA, 5 µl of 10× reaction buffer, 200 µM dNTP, 200 nM of each primer, and 1 µl of 50× Advantage-GC2 DNA polymerase mixture (Clontech, CA). The PCR reaction parameter was: initial denaturing at 94° C. for 1 min, followed by 30 cycles of denaturing at 94° C. for 30 sec, annealing at 55° C. for 30 sec and extension at 72° C. for 2 min. After PCR, the 0.6 kb PCR fragment was purified, polished and subcloned into pPCRscript. About twenty independent clones were picked, their plasmid DNA was isolated, and sequenced.

The double-stranded DNA sequencing analysis revealed that there exist three types of COX-3 splicing variants in human tissues. The first type (Type I) is one in which the entire 94 bp of intron 1 is retained, leading to a shift in the reading frame, which encodes a very short peptide that is likely a COX-inactive protein. The second type (Type II or COX-3a, FIG. 1C) retains almost the entire intron 1 but is missing a guanidine at position 64, leading to a short and self-rectifying shift in the reading frame, which encodes a full length and COX-active protein. The amino terminal nucleotide sequence of the COX-3a is depicted in SEQ ID NO:3, and the amino acid sequence encoded by SEQ ID NO:3 is depicted in SEQ ID NO:4. Like Type II splicing variant, the third type (Type III or COX-3b, FIG. 1D) also retains almost the entire intron 1 but is missing a cytosine at bp position 43, leading to another short and self-rectifying shift in the reading frame, which encodes a full-length and COX-active protein. COX-3b encodes a protein that is slightly different from Cox-3a at its N-terminal ends. The amino terminal nucleotide sequence of the COX-3b is depicted in SEQ ID NO:5, and the amino acid sequence encoded by SEQ ID NO:5 is depicted in SEQ ID NO:6.

These results demonstrated the existence of human Cox-3, suggesting that human COX-3 can be formed via one or more than one RNA editing events following the retention of intron 1. The N-terminal of hCox-3a or hCox-3b, encoded by the retention of human Cox-1 intron 1 is significantly different from that of the canine, exhibiting about 33% or 26% sequence identity (FIG. 1E) to that of the canine Cox-3, respectively. The nucleotide sequence of human COX-1 intron 1 shares about 75% sequence identity to that of the canine COX-1 intron 1 (Chandrasekharan et al., 2002, supra).

EXAMPLE 3

Genomic Structure and Splicing Variants of Human COX-1 and COX-3

The full-length cDNA sequence of the human COX-1 and COX-3 genes were used to search the Genbank human genome database. The search indicated that the gene encoding the human COX-1/COX-3 protein is about 22 kb and localized on chromosome 9. As shown in FIG. 2, the gene encoding the human COX-1 protein is composed of 11 exons and 10 introns. The COX-1 is encoded by Exon 1 through Exon 11, while the novel splicing variant, COX-3, is encoded by same number of exons plus a retained intron 1 between exon 1 and exon 2, which, after RNA editing, results in a 31 residue insertion at the amino terminus.

EXAMPLE 4

Assembly of Full-Length Human COX-3

To assemble the full-length human COX-3, a carboxyl terminal cDNA fragment was first amplified from Marathon-Ready™ human brain cDNA library (BD Bioscience Clontech, Palo Alto, Calif.) with two human COX-1 specific primers: forward primer, SEQ ID NO: 12, 5' CAT ATG AGC CGG AGT CTC TTG CTC TGG TTC, 3', and reverse primer, containing a SalI restriction enzyme site, SEQ ID NO: 13, 5' GTC GAC TCA GAG CTC TGT GGA TGG TCG CTC CAC 3'. The PCR was performed in a final volume of 50 µl, containing 5 µl of Marathon-Ready™ human brain cDNA, 5 µl of 10× reaction buffer, 200 µM of dNTPs, 200 µM specific primers, and 1 µl of 50× Advantage HF2 DNA polymerase mixture (Clontech). The PCR reaction parameters were: initial denaturing at 94° C. for 1 min, followed by 30 cycles of denaturing at 94° C. for 30 sec, annealing at 55° C. for 30 sec and extension at 72° C. for 2 min. After PCR, the 1.75 kb PCR fragment was purified, digested with EcoRI and SalI, separated on a 1% agarose gel, and finally, a 1.55 kb carboxyl terminal fragment was excised.

The full-length human COX-3a cDNA was assembled and subcloned into pAGA4 vectors according to standard molecular biology methods. Briefly, the 0.33 kb N-terminal fragment from bp position 1 (NdeI site with start codon) to bp position 332 (EcoRI site) and the 1.55 kb C-terminal fragment (from EcoRI to SalI, see above) were directly subcloned into a pAGA4 vector predigested by NdeI and SalI. The resulting construct was designated hCOX-3/pAGA4. The final construct was confirmed by DNA sequencing. The nucleotide sequence of the full-length human COX-3a cDNA is depicted in SEQ ID NO: 8, and the amino acid sequence of the full length human COX-3a is depicted in SEQ ID NO: 9.

Following similar procedure, the full-length human Cox-3b cDNA can also be assembled. The nucleotide sequence of the full-length human COX-3b cDNA is depicted in SEQ ID NO: 10, and the amino acid sequence of the full length human COX-3b is depicted in SEQ ID NO: 11.

EXAMPLE 5

In Vitro Translational Analysis of Human COX-3a and COX-1 Proteins

In vitro translation of the human COX-3a and COX-1 proteins were performed with the TnT® T7 Quick Coupled Transcription/Translation System (Promega) according to the vendor recommended protocol. Briefly, 1 µl of 0.1 µg/µl hCOX-3/pAGA4 and hCOX-1/pAGA4 constructs were added to 9 µl of TNT Quick Master Mix with 0.2 µl of [$^{35}$S]methionine (1000 Ci/mmol at 10 mCi/ml). The reaction mixture was incubated at 30° C. for 90 min. The reactions were stopped by adding an equal volume of 2× SDS-PAGE loading buffer and then, the samples were subjected to 10-20% gradient SDS-PAGE separation. After electrophoresis, the gel was stained with Coomassie Blue R250, dried and exposed to X-ray film. The in vitro translated human COX-3a protein was slightly larger than the COX-1 protein, and both migrated to an estimated molecular weight of about 70 kDa, as predicted by translation of the amino acid sequences from the corresponding nucleic acid sequences.

The in vitro translated human COX-3a and COX-1 proteins were also analyzed by Western blot. Briefly, 2 µl of in vitro translated human COX-3 and COX-1 proteins were subjected to 10-20% gradient SDS-PAGE. The proteins on the gel were then transferred to nitrocellulose. The blot was blocked with 5% dry milk in TTBS (0.5% Tween 20, 100 mM Tris-HCl, and 0.9% NaCl at pH=7.5) at room temperature for 1 hour and then incubated with a 1:500 dilution of anti-human COX-1 monoclonal antibody (Sigma) at 4° C. overnight. The next day, the blot was washed three times with 100 ml TTBS, and incubated with goat anti-mouse IgG antibody conjugated to horseradish peroxidase (Pierce) at room temperature for 1 hour. After washing three times with 100 ml TTBS, the blot was visualized with the luminescent reagent ECL-Plus (Amersham-Pharamacial Biotech). The result of the Western blot was consistent with that from the in vitro translational analysis.

EXAMPLE 6

Northern Blot Analysis of the Human COX-3 Expression

Northern blot analysis was used to assess the tissue distribution of the human COX-3. An antisense oligonucleotide hcx1-12, corresponding to bp 34-71 (within intron 1) of COX-3 was used as a probe. The nucleotide sequence of hcx1-12, SEQ ID 14, is 5'-TGGCATTCAAGGCTCCAC-CAGGAGGCCAAGAAAATTCC-3'. The oligonucleotide probe was 5'-end labeled by [γ-$^{32}$P] ATP. Briefly, 10 pmol hcx1-12 oligonucleotide was incubated at 37° C. for 30 minutes in the presence of 3.5 µl of [γ-$^{32}$P]ATP at 6000 Ci/mmol (Amersham Pharmacia Biotech), 1 µl of 10 unit/µl T4 polynucleotide kinase (Roche Applied Science) and 2.5 µl 10× kinase buffer provided by the vendor in a total volume of 25 µl. The reaction was stopped by the addition of 5 µl of 0.5 M EDTA. The labeled probe was then purified using a CHROMA SPIN+STE-30 Column (Clontech, CA) according to the vendor's protocol.

Human MTN (Multiple Tissue Northern) blots were purchased from Clontech (Palo Alto, Calif.). They are Human MTN blot (Cat. No. 7760-1), Human II MTN blot (Cat. No. 7767-1), Human III MTN blot (Cat. No. 7767-1) and human tumor MTN blot (Cat. No. 7792-1). Each blot was prehybridized with 5 ml ExpressHyb Solution (Clontech) at 42° C. for 30 minutes, and then hybridized in the presence of 2×10$^6$ cpm/µl of the human COX-3 oligonucleotide probe at 42° C. for 2 hours. The blots were rinsed with 2×SSC/0.05% SDS and then washed twice with 200 ml of 0.1×SSC/0.1% SDS solution at room temperature for two hours. Finally the blots were exposed to X-ray film in a −80° C. freezer up to 3 days.

Northern blot analysis demonstrates that the major transcript of human COX-3 is about 4.5 kb. The 4.5 kb COX-3 transcript is most abundant in human stomach, followed by skeletal muscle, heart, placenta, liver, pancreas, spleen, testis, adrenal gland and kidney. It is also expressed at a relatively low levels in brain, lung, prostate, small intestine, leukocyte, thyroid, spinal cord, lymph node and trachea. No significant transcript was observed in thymus, ovary, colon or bone marrow. Interestingly, the level of 4.5 kb human COX-3 transcript was found to be dramatically increased in all the human tumor tissues we tested, suggesting that it may play a role in carcinogenesis.

EXAMPLE 7

Generation of Polyclonal Antibodies Specific to hCox-3

An oligopeptide sequence derived from amino terminus of human COX-3a and Cox-3b was selected in order to raise polyclonal antibodies in rabbits. For better coupling, the internal cysteine in the peptide was changed to a serine. The amino acid sequence for the oligopeptide was SEQ ID NO: 15, Ac-MSRECDPGARWGC-amide.

The peptide was synthesized and antibodies were raised and purified by BioSource International, Inc. The resulting antibodies were tested by ELISA against the antigen peptide and affinity purified with the same peptide. Serum and affinity purified antibodies were used for immunoanalysis, including Western blot, immunoprecipitation, immuno-PCR, immunocytochemistry and immunohistochemistry.

EXAMPLE 8

Western Blot Analysis of Human COX-3 Expression

To analyze human COX-3 protein expression, a specific anti-human COX-3 polyclonal antibody was generated and affinity purified as described in Example 7. A pre-made human multiple tissue total protein blot was purchased from Biochain (CA). Briefly, the premade blot was blocked with 5% dry milk in TTBS (0.5% Tween 20/100 mM NaCl/10 mM Tris-HCl at pH=7.4) for 2 hours at room temperature and then incubated with a 1:1000 dilution of affinity purified anti-human COX-3 antibody in 5% dry milk/TTBS at 4° C. overnight. A 1:10,000 dilution of secondary goat anti-rabbit IgG conjugated with HRP (Pierce) was applied to the blot for 1 hour at RT. Finally, the signals were visualized on X-ray film using the ECL-plus kit (Amersham).

The results showed that two major immunoreactive proteins, 80 and 55 kDa, respectively, were identified in human total protein lysates. The 80 kDa protein, presumably representing human COX-3a or -3b, is expressed in heart, brain, kidney, liver, skeletal muscle, stomach and small intestine. The 55 kDa protein, which is similar to another COX-1 splicing variant, PCOX-1a, described by Chandrasekharan et al. (*PNAS,* 2002, Vol. 99, pp 13926), is expressed more broadly in the human tissues that were tested. Several smaller uncharacterized proteins were also identified.

EXAMPLE 9

Recombinant Expression of Human COX-3a in Insect Sf9 Cells

For structural and functional studies, the full length human COX-3a cDNA was subcloned into pFastBac (Invitrogen, CA), a baculovirus expression donor vector. The recombinant Bacmid was made in DH10Bac *E. coli* cells after transposition of the construct. The high titer (1×10$^9$ pfu/ml) of recombinant baculovirus was obtained after transfection with recombinant Bacmid and subsequently amplified twice. A distinguished peptide band, migrating at about 75 kDa, was observed in SDS-PAGE gels stained by Coomassie blue R250, the identity of which was further confirmed by Western blot using the anti-COX-1 monoclonal antibody.

EXAMPLE 10

COX Activity Assay

Microsomal protein fractions were prepared from Sf9 cells infected with the hCOX-3a recombinant baculovirus. Microsomal membrane protein (20 µg) was incubated with the indicated concentration of arachidonic acid in a volume of 150 µl buffer containing 0.1 M Tris-HCl (pH=8.0), 5 mM EDTA, 2 mM phenol and 1.5 µM hamatin. After incubating at room temperature for 5 minutes, the reaction was terminated by the addition of 40 µl of 1 N HCl with mixing. Samples were neutralized with 40 µl of 1 N NaOH. The formation of the $PGF_{2\alpha}$ product was determined using a $PGF_{2\alpha}$ immunoassay kit (Assay Designs, Inc.), as directed by the manufacturer.

Figure 3:
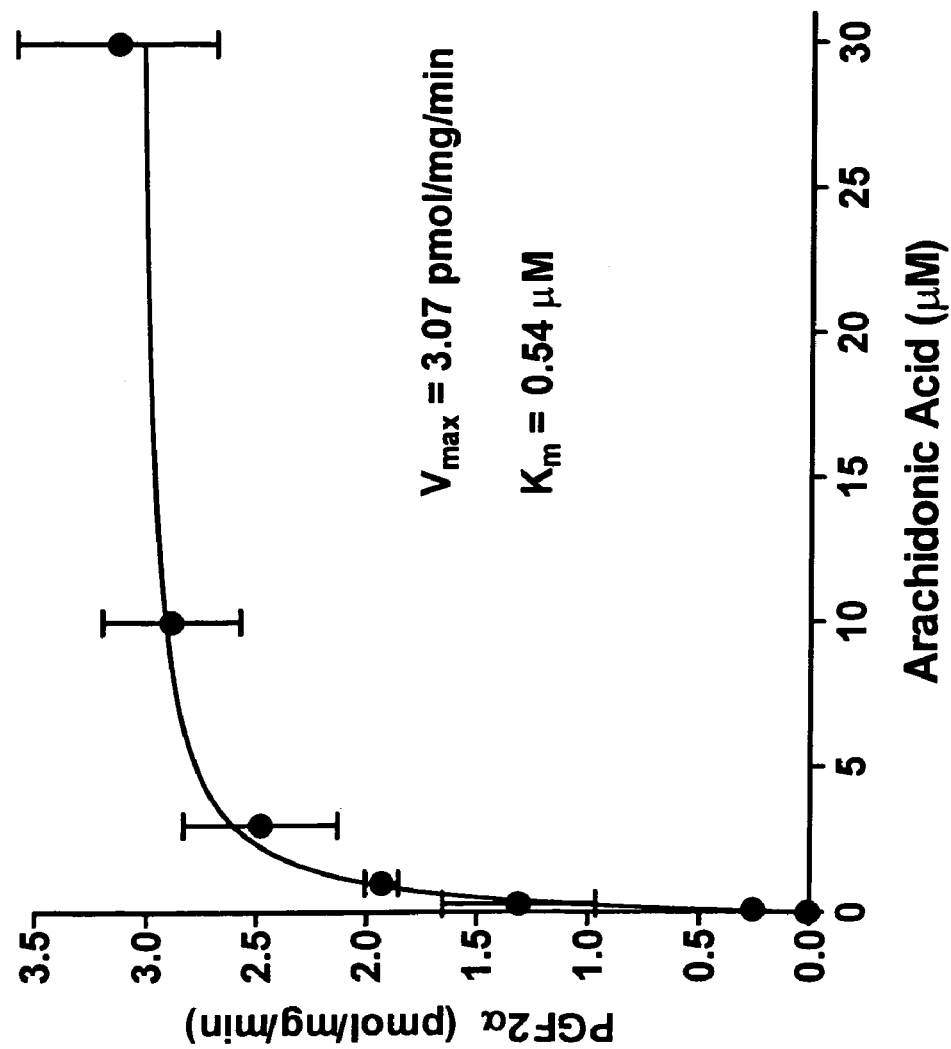
FIG. 3 shows that human Cox-3a protein catalyzed the synthesis of PGF2a from arachidonic acid.

Like COX-1 and COX-2, human COX-3a was able to catalyze the synthesis of $PGF_{2\alpha}$ from arachidonic acid in a concentration-dependent manner, with $K_m$ and $V_{max}$ values of 0.54 µM and 3.07 pmol/mg/min, respectively (FIG. 3).

Although the various aspects of the invention have been illustrated above by reference to examples and preferred embodiments, it will be appreciated that the scope of the invention is defined not by the foregoing description, but by the following claims properly construed under principles of patent law.

---

What is claimed is:

1. An isolated polynucleotide comprising the DNA sequence of SEQ ID NO: 8 encoding a full-length polypeptide of SEQ ID NO: 9 having cyclooxygenase-3 activity, said polypeptide further comprising within the full-length polypeptide an insertion of 31 amino acid residues of SEQ ID NO:4 at the amino terminus encoded by the polynucleotide sequence of SEQ ID NO: 3.

2. An expression vector comprising the polynucleotide of claim 1.

3. An isolated host cell comprising the expression vector of claim 2.

* * * * *